United States Patent
Park et al.

(10) Patent No.: US 9,054,321 B2
(45) Date of Patent: Jun. 9, 2015

(54) HETEROCYCLIC COMPOUND AND ORGANIC LIGHT-EMITTING DEVICE CONTAINING THE SAME

(75) Inventors: Bum-Woo Park, Yongin (KR); Yoon-Hyun Kwak, Yongin (KR); Sun-Young Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 499 days.

(21) Appl. No.: 13/365,402

(22) Filed: Feb. 3, 2012

(65) Prior Publication Data

US 2013/0092903 A1 Apr. 18, 2013

(30) Foreign Application Priority Data

Oct. 18, 2011 (KR) ........................ 10-2011-0106633

(51) Int. Cl.
 *H01L 51/50* (2006.01)
 *H01L 51/00* (2006.01)
 *C07D 487/06* (2006.01)

(52) U.S. Cl.
 CPC ............ *H01L 51/006* (2013.01); *C07D 487/06* (2013.01); *H01L 51/0081* (2013.01); *H01L 51/5012* (2013.01); *H01L 2251/308* (2013.01)

(58) Field of Classification Search
 None
 See application file for complete search history.

(56) References Cited

U.S. PATENT DOCUMENTS

| | | | |
|---|---|---|---|
| 5,635,308 A | 6/1997 | Inoue et al. | |
| 5,645,948 A | 7/1997 | Shi et al. | |
| 5,972,247 A | 10/1999 | Shi et al. | |
| 6,114,805 A * | 9/2000 | Codama et al. | 313/509 |
| 6,465,115 B2 | 10/2002 | Shi et al. | |

(Continued)

FOREIGN PATENT DOCUMENTS

| | | |
|---|---|---|
| JP | 8-12600 A | 1/1996 |
| JP | 2000-3782 A | 1/2000 |

(Continued)

OTHER PUBLICATIONS

Organic electroluminescent diodes by C.W. Tang and S.A. VanSlyke. (Received May 12, 1987; accepted for publication Jul. 20, 1987).

(Continued)

*Primary Examiner* — Gregory Clark
(74) *Attorney, Agent, or Firm* — Robert E. Bushnell, Esq.

(57) ABSTRACT

A heterocyclic compound represented by Formula 1, and an organic layer including the heterocyclic compound:

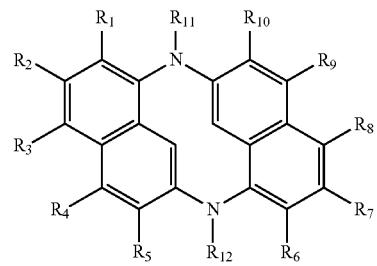

wherein Formula 1 is as defined in the specification. The organic light-emitting device including the heterocyclic compound has high efficiency, low driving voltage, high brightness, and long lifespan.

20 Claims, 1 Drawing Sheet

(56) References Cited

U.S. PATENT DOCUMENTS

| | | | |
|---|---|---|---|
| 6,596,415 B2 | 7/2003 | Shi et al. | |
| 2003/0118866 A1* | 6/2003 | Oh et al. | 428/690 |
| 2007/0090362 A1* | 4/2007 | Ahn et al. | 257/66 |
| 2008/0176099 A1* | 7/2008 | Hatwar et al. | 428/690 |
| 2008/0182129 A1 | 7/2008 | Klubek et al. | |
| 2009/0072716 A1 | 3/2009 | Funahashi | |
| 2011/0240979 A1* | 10/2011 | Kim et al. | 257/40 |

FOREIGN PATENT DOCUMENTS

| | | |
|---|---|---|
| KR | 10-2007-0101752 A | 10/2007 |
| KR | 10-2008-0005227 A | 1/2008 |
| KR | 10-2009-0122192 A | 11/2009 |
| KR | 10-2010-0003624 A | 1/2010 |

OTHER PUBLICATIONS

Confinement of charge carriers and molecular excitons within 5-nm-thick emitter layer in organic electroluminescent with a double heterostructure by Chihaya Adachi et al. (Received Jan. 29, 1990; accepted for publication May 30, 1990).

J. Am. Chem. Soc. 2000, 122, 1832-1833 by Youichi Sakamoto et al. (Received Nov. 22, 1999; published on Web Feb. 15, 2000).

Chemistry Letters 2001: Diphenylamino-Substituted 2,5-Diarylsiloles for Single-lyer organic Electroluminescent Devices by Shigehiro Yamaguchi et al. (Received Nov. 10, 2000; CL-001026).

* cited by examiner

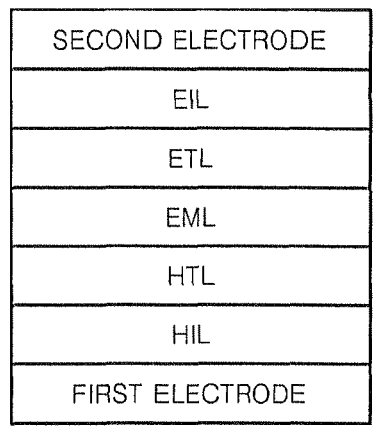

HETEROCYCLIC COMPOUND AND ORGANIC LIGHT-EMITTING DEVICE CONTAINING THE SAME

CROSS-REFERENCE TO RELATED PATENT APPLICATION

This application makes reference to, incorporates the same herein, and claims all benefits accruing under 35 U.S.C. §119 from an application earlier filed in the Korean Intellectual Property Office on 18 Oct. 2011 and there duly assigned Serial No. 10-2011-0106633.

BACKGROUND OF THE INVENTION

1. Field of the Invention

The present invention relates to a heterocyclic compound represented by Formula 1 and an organic light-emitting device including the heterocyclic compound.

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers (EMLs) containing inorganic compounds, and organic light-emitting devices that include EMLs containing organic compounds. Specifically, organic light-emitting devices have higher brightness, lower driving voltages, and shorter response times than inorganic light-emitting devices, and can render multi-colored displays. Thus, much research into such organic light-emitting devices has been conducted. Generally, an organic light-emitting device has a stack structure including an anode, a cathode, and an organic EML interposed therebetween. However, a hole injection layer (HIL) and/or a hole transport layer (HTL) may further be stacked between the anode and the organic EML, and/or an electron transport layer (ETL) may further be stacked between the organic EML and the cathode. In other words, an organic light-emitting device may have a stack structure of anode/HTL/organic EML/cathode or a stack structure of anode/HTL/organic EML/ETL/cathode.

As a material for the organic EML, an anthracene derivative has been used. However, organic light-emitting devices including such a known organic emission material do not have satisfactory life span, efficiency, and power consumption characteristics, thereby improvement in this regard still being necessary.

SUMMARY OF THE INVENTION

The present invention provides a heterocyclic compound having excellent electrical characteristics, charge transporting capabilities, and light-emission capabilities.

The present invention also provides an organic light-emitting device including the heterocyclic compound.

The present invention also provides a flat panel display device including the organic light-emitting device.

According to an aspect of the present invention, there is provided a compound represented by Formula 1 below:

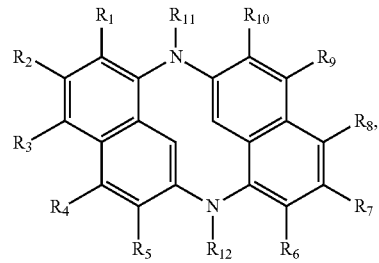

wherein, in Formula 1, $R_1$ through $R_{12}$ are each independently a hydrogen atom, a heavy hydrogen atom, a halogen atom, a cyano group, a substituted or unsubstituted $C_1$-$C_{60}$ alkyl group, a substituted or unsubstituted $C_1$-$C_{60}$ alkenyl group, a substituted or unsubstituted $C_5$-$C_{60}$ aryl group, an amino group substituted with a $C_5$-$C_{50}$ aryl group, a substituted or unsubstituted $C_3$-$C_{60}$ heteroaryl group, or a substituted or unsubstituted $C_6$-$C_{60}$ condensed polycyclic group, and wherein, optionally, adjacent substituents from among $R_1$ through $R_5$ or adjacent substituents from among $R_6$ through $R_{10}$ are connected to each other to form a ring.

In Formula 1, $R_1$ to $R_{12}$ may be each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, a substituted or unsubstituted $C_5$-$C_{30}$ aryl group, an amino group substituted with a $C_5$-$C_{30}$ aryl group, a substituted or unsubstituted $C_3$-$C_{30}$ heteroaryl group, or a substituted or unsubstituted $C_6$-$C_{30}$ condensed polycyclic group aryl group.

In Formula 1, $R_1$ to $R_{12}$ may be each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, and one of Formulae 2a to 2i below:

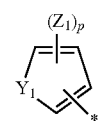

2a

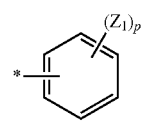

2b

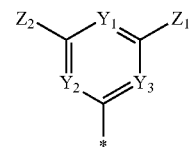

2c

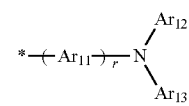

2d

-continued

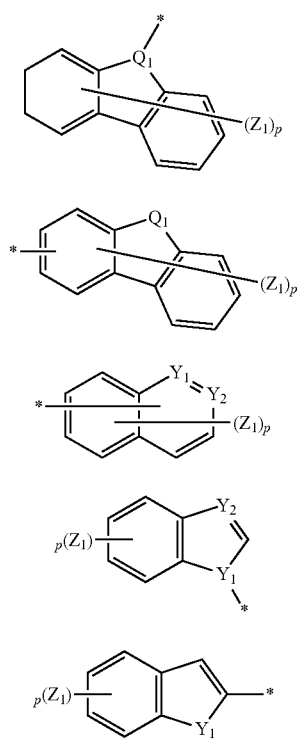

2e

2f

2g

2h

2i wherein, in Formulae 2a to 2i, $Q_1$ may be represented by —$C(R_{13})(R_{14})$—, —$N(R_{15})$—, —N(—*)—, —S—, or —O—; $Y_1$, $Y_2$, and $Y_3$ may be each independently represented by —N=, —N(—*)—, —S—, —O—, —$C(R_{16})$=, or —C(—*)=; $Z_1$, $Z_2$, $Ar_{12}$, $Ar_{13}$, $R_{13}$, $R_{14}$, $R_{15}$, and $R_{16}$ may be each independently selected from the group consisting of a lone pair electron, a hydrogen atom, a heavy hydrogen atom, a halogen atom, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxyl group, and a carboxyl group; $Ar_{11}$ may be selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group; p may be an integer from 1 to 10; r may be an integer from 0 to 5; and * may indicate a binding site.

In Formula 1, $R_1$ to $R_{12}$ may each be independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, and one of Formulae 3a to 3d below:

-continued

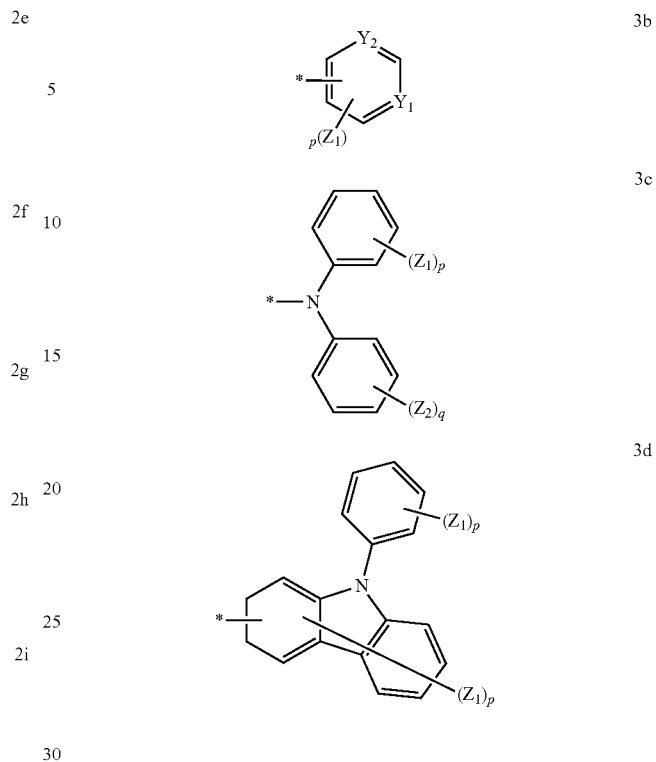

3b

3c

3d wherein, in Formulae 3a to 3d, $Y_1$ and $Y_2$ may each be represented by —N= or —$C(R_{16})$=; $Z_1$ and $Z_2$ may be selected from the group consisting of a hydrogen atom, a heavy hydrogen atom, a halogen atom, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group; p and q may each be an integer from 1 to 5; and * may indicate a binding site.

The compound represented by Formula 1 may be a symmetrical compound.

In Formula 1, $R_1$ to $R_{12}$ may be each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, and one of Formulae 2a to 2i below, and the compound represented by Formula 1 is a symmetrical compound:

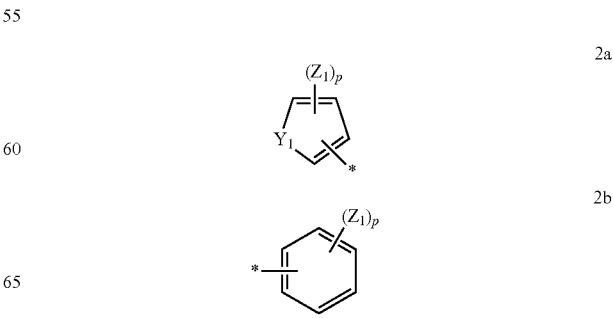

2a

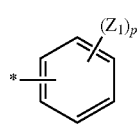

3a

2b

-continued

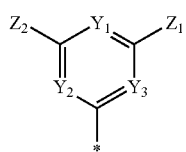
2c

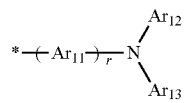
2d

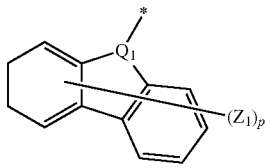
2e

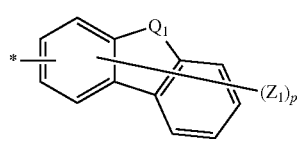
2f

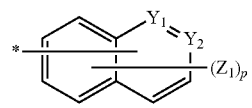
2g

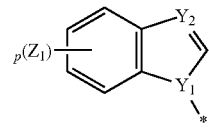
2h

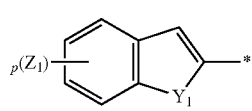
2i wherein, in Formulae 2a through 2i, $Q_1$ may be represented by —$C(R_{13})(R_{14})$—, —$N(R_{15})$—, —N(—*)-, —S—, or —O—; $Y_1$, $Y_2$, and $Y_3$ may be each independently represented by —N═, —N(—*)-, —S—, —O—, —$C(R_{16})$═, or —C(—*)═; $Z_1$, $Z_2$, $Ar_{12}$, $Ar_{13}$, $R_{13}$, $R_{14}$, $R_{15}$, and $R_{16}$ are each independently selected from the group consisting of a lone pair electron, a hydrogen atom, a heavy hydrogen atom, a halogen atom, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group; $Ar_{11}$ is selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group; p is an integer from 1 to 10; r is an integer from 0 to 5; and * indicates a binding site.

The compound represented by Formula 1 may include any one of Compounds below:

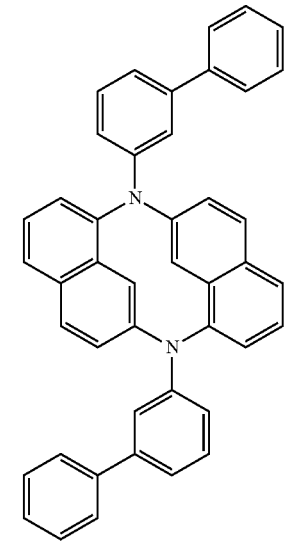
4

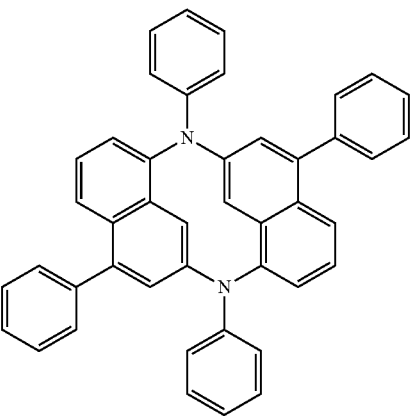
17

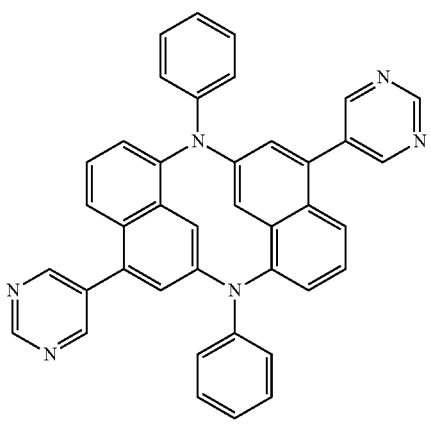
21

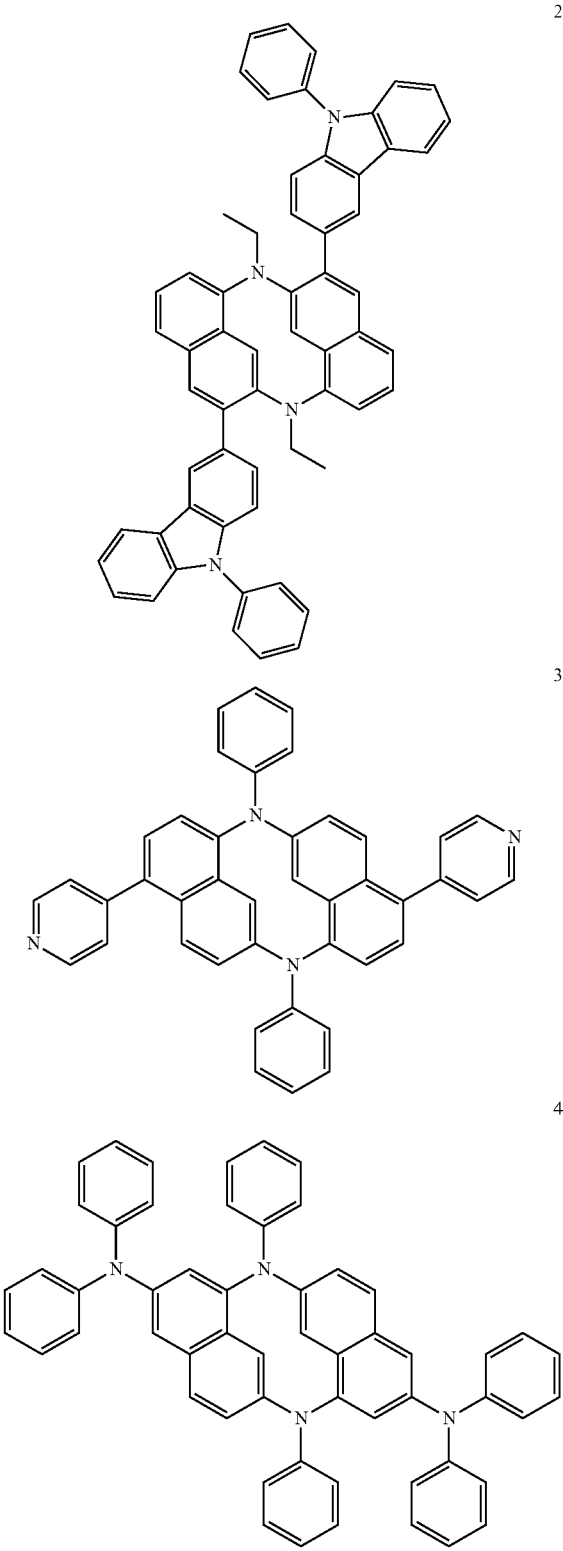

According to another aspect of the present invention, there is provided an organic light-emitting device including a first electrode; a second electrode; and an organic layer interposed between the first electrode and the second electrode, wherein the organic layer includes a first layer including the compound represented by Formula 1.

The first layer may include a hole injection layer (HIL), a hole transport layer (HTL), a functional layer having both hole injecting and hole transporting capabilities, an electron injection layer (EIL), an electron transporting layer (ETL), or a functional layer having both electron injecting and electron transporting capabilities.

The first layer may be a light-emitting layer (EML), and the compound represented by Formula 1 may be used as a host for a fluorescence or phosphorescence device.

The organic layer may include an EML, an HTL, and an ETL, the first layer may be the EML, and the EML may further include an anthracene compound, an arylamine compound, or a styryl compound.

The organic layer may include an EML, an HTL, and an ETL, the first layer may be the EML, and any one of a red layer, a green layer, a blue layer, and a white layer of the EML may further include a phosphorescent compound.

The first layer may be a blue EML.

The first layer may be a blue EML; and the compound represented by Formula 1 may be used as a blue host.

The organic layer may include a HIL, a HTL, a functional layer having both hole injecting and hole transporting capabilities, an EML, a hole blocking layer (HBL), an ETL, an EIL, or a combination of at least two thereof.

At least one of the HIL, the HTL, and the functional layer having both hole injecting and hole transporting capabilities may include a charge-generating material.

The ETL may include an electron-transporting organic compound and a metal-containing material.

The metal-containing material may include a lithium (Li) complex.

The first layer may be formed by using a wet method using the above-described compound.

According to another aspect of the present invention, there is provided a flat panel display device including the above-described organic light-emitting device, wherein the first electrode of the organic light-emitting device is electrically connected to a source electrode or a drain electrode of a thin film transistor.

BRIEF DESCRIPTION OF THE DRAWING

The above and other features and advantages of the present invention will become more apparent by describing in detail exemplary embodiments thereof with reference to the attached drawing in which:

FIG. 1 illustrates an organic light-emitting device according to an embodiment of the present invention.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

It will be understood that when an element such as a layer, film, region, or substrate is referred to as being "on" another element, it can be directly on the other element or intervening elements may also be present. In contrast, when an element is referred to as being "directly on" another element, there are no intervening elements present.

Anthracene derivatives are widely known as materials for forming an organic emission layer (EML). 2-biphenyl-4-yl-5-(4-tert-butyl-phenyl)-[1,3,4]oxadiazole (PBD), perfluoronated chemical (PF-6P), and 2,5-bis(6'-(2',2"-bipyridyl))-1,1-dimethyl-3,4-diphenylsiylol (PyPySPyPy), as well as tris (8-quinolinorate)aluminum (Alq3), are also widely known as materials for forming an electron transport layer (ETL). For example, an organic light-emitting device manufactured using a compound of phenylanthracene dimer or trimer is widely known. However, such organic light-emitting devices have a narrow energy gap and lower blue-light color purity since two or three oligomeric species of anthracene are linked by conjugation.

In addition, such compounds are highly vulnerable to oxidation and thus are liable to produce impurities, necessitating purification. In order to overcome these drawbacks, organic light-emitting devices manufactured using an anthracene compound including naphthalene substituted for anthracene at 1,9 position or using a diphenylanthracene compound including an aryl group substituted for a phenyl group at m-position have been introduced. However, these organic light-emitting devices have lower light-emission efficiency.

In addition, organic light-emitting devices manufactured using a naphthalene-substituted monoanthracene derivative have been introduced. However, the compound has a low light-emission efficiency of about 1 cd/A, and thus such organic light-emitting devices are not suitable for practical use. Organic light-emitting devices manufactured using compounds having a phenylanthracene structure have been introduced. However, these compounds are substituted with an aryl group at m-position, and thereby having a low light-emission efficiency of about 2 cd/A in spite of excellent thermal resistance.

The present invention will now be described in more detail.

According to an embodiment of the present invention, a heterocyclic compound represented by Formula 1 below is provided.

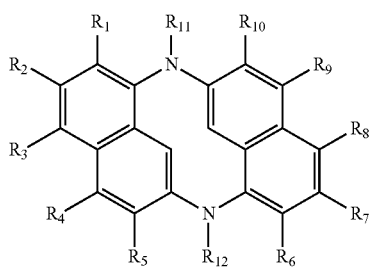

Formula 1

In Formula 1, $R_1$ through $R_{12}$ are each independently a hydrogen atom, a heavy hydrogen atom, a halogen atom, a cyano group, a substituted or unsubstituted $C_1$-$C_{60}$ alkyl group, a substituted or unsubstituted $C_1$-$C_{60}$ alkenyl group, a substituted or unsubstituted $C_5$-$C_{60}$ aryl group, an amino group substituted with a $C_5$-$C_{50}$ aryl group, a substituted or unsubstituted $C_3$-$C_{60}$ heteroaryl group, or a substituted or unsubstituted $C_6$-$C_{60}$ condensed polycyclic group, and optionally, adjacent substituents from among $R_1$ through $R_5$ or adjacent substituents from among $R_6$ through $R_{10}$ may be connected to each other to form a ring.

The heterocyclic compound of Formula 1 according to an embodiment of the present embodiment may be suitable as a material for forming an EML, an ETL, or an electron injection layer (EIL) of an organic light-emitting device. The compound containing the heterocyclic compound represented by Formula 1 includes a hetero cycle and thus has a high glass transition temperature (Tg) or a high melting point. Thus, the heterocyclic compound has high thermal resistance against Joule's heat generated in an organic layer, between organic layers, or between an organic layer and a metallic electrode when light emission occurs, and has high durability in a high-temperature environment.

An organic light-emitting device manufactured using one of the compounds of Formula 1 has high durability when stored or operated.

A substituent in the compound of Formula 1 will now be described in detail.

In Formula 1, $R_1$ to $R_{12}$ may be each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, a substituted or unsubstituted $C_5$-$C_{30}$ aryl group, an amino group substituted with a C5-C30 aryl group, a substituted or unsubstituted $C_3$-$C_{30}$ heteroaryl group, or a substituted or unsubstituted $C_6$-$C_{30}$ condensed polycyclic group aryl group.

In Formula 1, $R_1$ to $R_{12}$ may be each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, and one of Formulae 2a to 2i below:

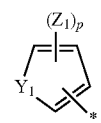

2a

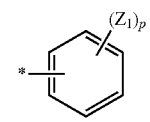

2b

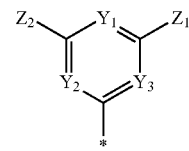

2c

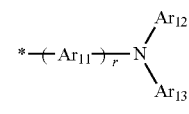

2d

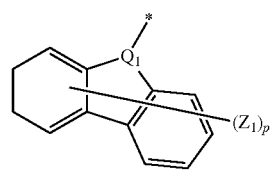

2e

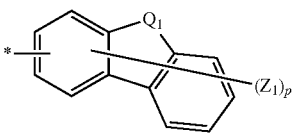

2f

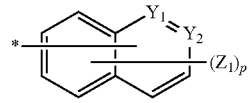

2g

-continued

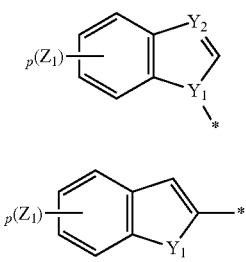

2h

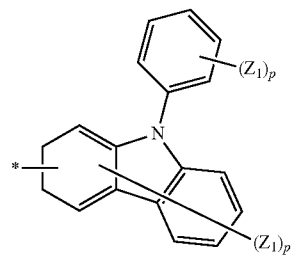

3d

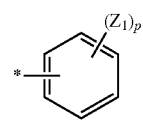

2i

In Formulae 2a to 2i, $Q_1$ is represented by —C($R_{13}$)($R_{14}$)—, —N($R_{15}$)—, —N(—*)—, —S—, or —O—; $Y_1$, $Y_2$, and $Y_3$ are each independently represented by —N=, —N(—*)—, —S—, —O—, —C($R_{16}$)=, or —C(—*)=; $Z_1$, $Z_2$, $Ar_{12}$, $Ar_{13}$, $R_{13}$, $R_{14}$, $R_{15}$, and $R_{16}$ are each independently selected from the group consisting of a lone pair electron, a hydrogen atom, a heavy hydrogen atom, a halogen atom, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group; $Ar_{11}$ is selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group; p is an integer from 1 to 10; r is an integer from 0 to 5; and * indicates a binding site.

According to another example, in Formula 1, $R_1$ to $R_{12}$ are each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, and one of Formulae 3a to 3d below:

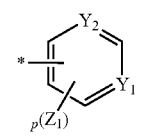

3a

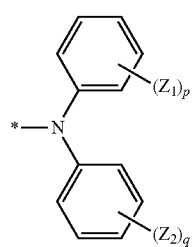

3b

3c

In Formulae 3a to 3d, $Y_1$ and $Y_2$ are each represented by —N= or —C($R_{16}$)=; $Z_1$ and $Z_2$ are selected from the group consisting of a hydrogen atom, a heavy hydrogen atom, a halogen atom, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group; p and q are each an integer from 1 to 5; and * indicates a binding site.

The compound represented by Formula 1 may be a symmetrical compound.

In Formula 1, $R_1$ to $R_{12}$ may be each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, and one of Formulae 2a to 2i below, and the compound represented by Formula 1 may be symmetrical compound:

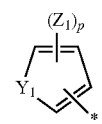

2a

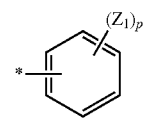

2b

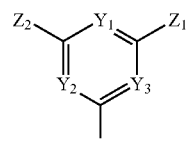

2c

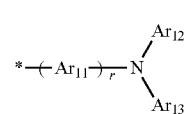

2d

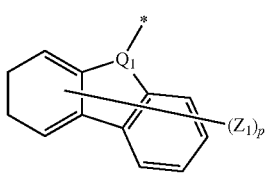

2e

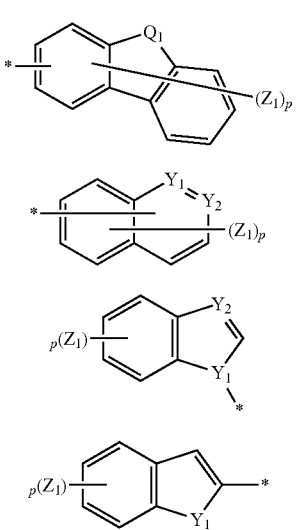

In Formulae 2a to 2i, $Q_1$ is represented by $—C(R_{13})(R_{14})—$, $—N(R_{15})—$, $—N(—*)-$, $—S—$, or $—O—$; $Y_1, Y_2,$ and $Y_3$ are each independently represented by $—N=$, $—N(—*)-$, $—S—$, $—O—$, $—C(R_{16})=$, or $—C(—*)=$; $Z_1, Z_2, Ar_{12}, Ar_{13}, R_{13}, R_{14}, R_{15},$ and $R_{16}$ are each independently selected from the group consisting of a lone pair electron, a hydrogen atom, a heavy hydrogen atom, a halogen atom, a cyano group, a substituted or unsubstituted $C_1$-$C_{20}$ alkyl group, a substituted or unsubstituted $C_5$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group; $Ar_{11}$ is selected from the group consisting of a substituted or unsubstituted $C_1$-$C_{20}$ alkylene group, a substituted or unsubstituted $C_5$-$C_{20}$ arylene group, and a substituted or unsubstituted $C_3$-$C_{20}$ heteroarylene group; p is an integer from 1 to 10; r is an integer from 0 to 5; and * indicates a binding site.

Hereinafter, substituents described with reference to Formulae 1 to 4 will now be described in detail. In this regard, the numbers of carbon atoms in substituents are presented only for illustrative purposes and do not limit the characteristics of the substituents.

The unsubstituted $C_1$-$C_{60}$ alkyl group used herein may be linear or branched. Examples of the alkyl group may include, but are not limited to, methyl, ethyl, propyl, isobutyl, sec-butyl, pentyl, iso-amyl, hexyl, heptyl, octyl, nonanyl, and dodecyl. At least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group used herein refers to a hydrocarbon chain having at least one carbon-carbon double bond within or at a terminal of the unsubstituted alkyl group. Examples of the $C_2$-$C_{60}$ alkenyl group include ethenyl, propenyl, and butenyl. At least one hydrogen atom of the alkenyl group may be substituted with the same substituent groups as described above in connection with the alkyl group.

The unsubstituted $C_2$-$C_{60}$ alkynyl group used herein refers to a hydrocarbon chain having at least one carbon-carbon triple bond within or at a terminal of the alkyl group. Examples of the unsubstituted $C_2$-$C_{60}$ alkynyl group include acetylene, propylene, phenylacetylene, naphthylacetylene, isopropylacetylene, t-butylacetylene, and diphenylacetylene. At least one hydrogen atom of the alkynyl group may be substituted with the same substituent groups as described above in connection with the alkyl group.

The unsubstituted $C_3$-$C_{60}$ cycloalkyl group used herein refers to a $C_3$-$C_{60}$ cyclic alkyl group wherein at least one hydrogen atom in the cycloalkyl group may be substituted with the same substituent group described above in connection with the $C_1$-$C_{60}$ alkyl group.

The unsubstituted $C_1$-$C_{60}$ alkoxy group used herein is a group having a structure of —OA wherein A is an unsubstituted $C_1$-$C_{60}$ alkyl group as described above. Examples of the $C_1$-$C_{60}$ alkoxy group include methoxy, ethoxy, propoxy, isopropyloxy, butoxy, and pentoxy. At least one hydrogen atom of the alkoxy group may be substituted with the same substituent groups as described above in connection with the alkyl group.

The unsubstituted $C_5$-$C_{60}$ aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the same substituent groups described with reference to the $C_1$-$C_{60}$ alkyl group.

Examples of the substituted or unsubstituted $C_5$-$C_{60}$ aryl group include a phenyl group, a $C_1$-$C_{10}$ alkylphenyl group (for example, ethylphenyl group), a halophenyl group (for example, o-, m-, and p-fluorophenyl group, and dichlorophenyl group), a cyanophenyl group, a dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, an o-, m-, and p-toryl group, an o-, m-, and p-cumenyl group, a mesityl group, a phenoxyphenyl group, an (α,α-dimethylbenzene) phenyl group, an (N,N'-dimethyl)aminophenyl group, an (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group used herein includes one, two or three hetero atoms selected from the group consisting of N, O, P and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. In addition, at least one hydrogen atom in the heteroaryl group may be substituted with the same substituent groups described above with reference to the $C_1$-$C_{60}$ alkyl group.

The unsubstituted $C_5$-$C_{60}$ aryloxy group used herein refers to a group represented by —$OA_1$, wherein $A_1$ is a $C_5$-$C_{60}$ aryl group. Examples of the aryloxy group include a phenoxy group. At least one hydrogen atom in the aryloxy group may be substituted with the same substituent groups described with reference to the $C_1$-$C_{60}$ alkyl group.

The unsubstituted $C_5$-$C_{60}$ arylthio group used herein refers to a group represented by —$SA_1$, wherein $A_1$ is a $C_5$-$C_{60}$ aryl group. Examples of the arylthio group include a benzenethio group and a naphthylthio group. At least one hydrogen atom in the arylthio group may be substituted with the substituent groups described with reference to the $C_1$-$C_{60}$ alkyl group.

The unsubstituted $C_6$-$C_{60}$ condensed polycyclic group is a substituent including at lest two rings wherein at least one aromatic ring and/or at least one non-aromatic ring are fused to each other.

Examples of the compound represented by Formula 1 may include Compounds 1 to 69 as shown below. However, the compound represented by Formula 1 is not limited thereto.

1
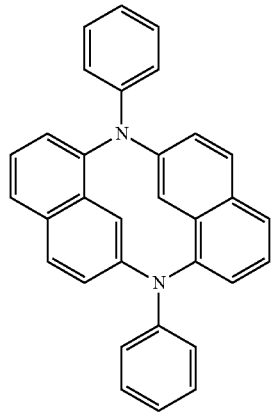

2
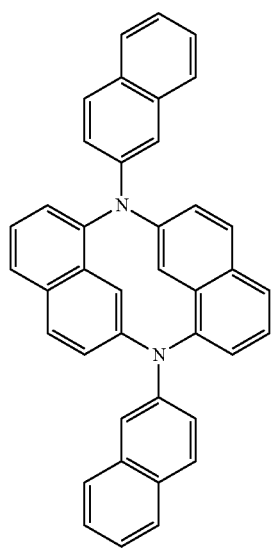

3
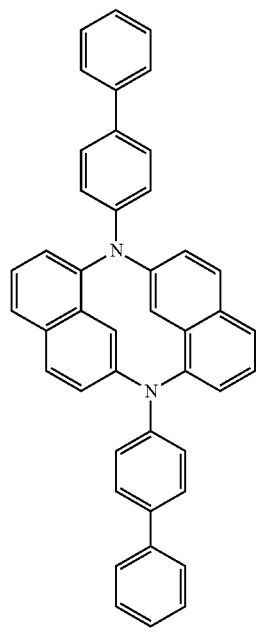

4
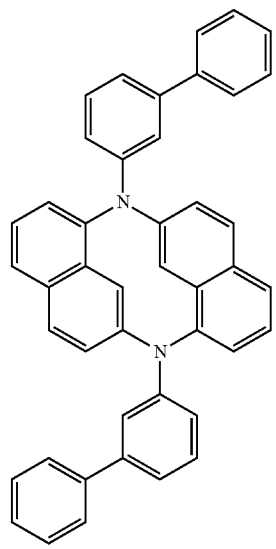

5
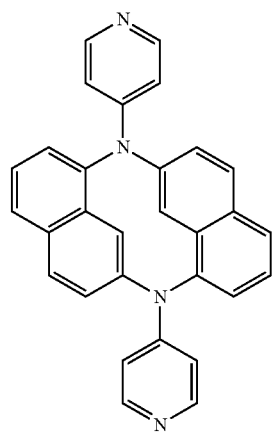

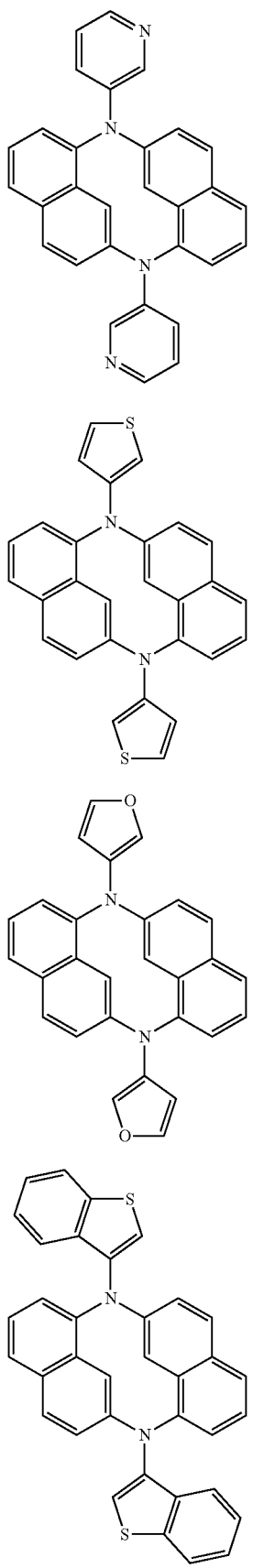
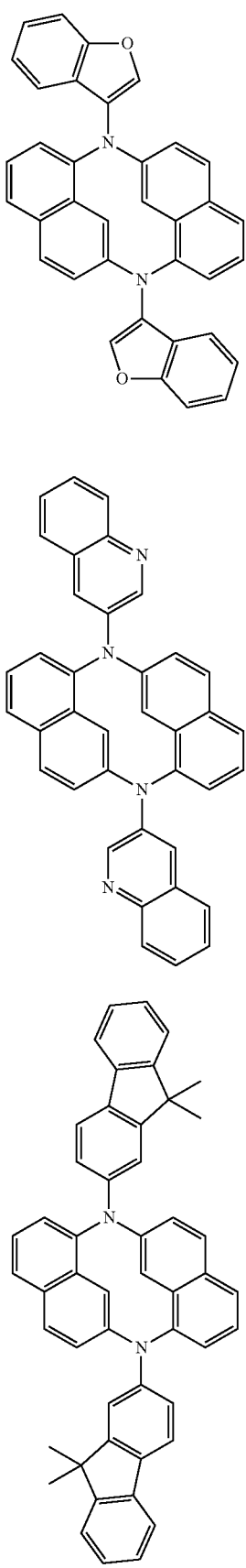

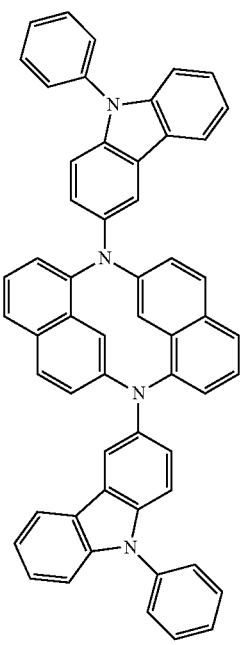
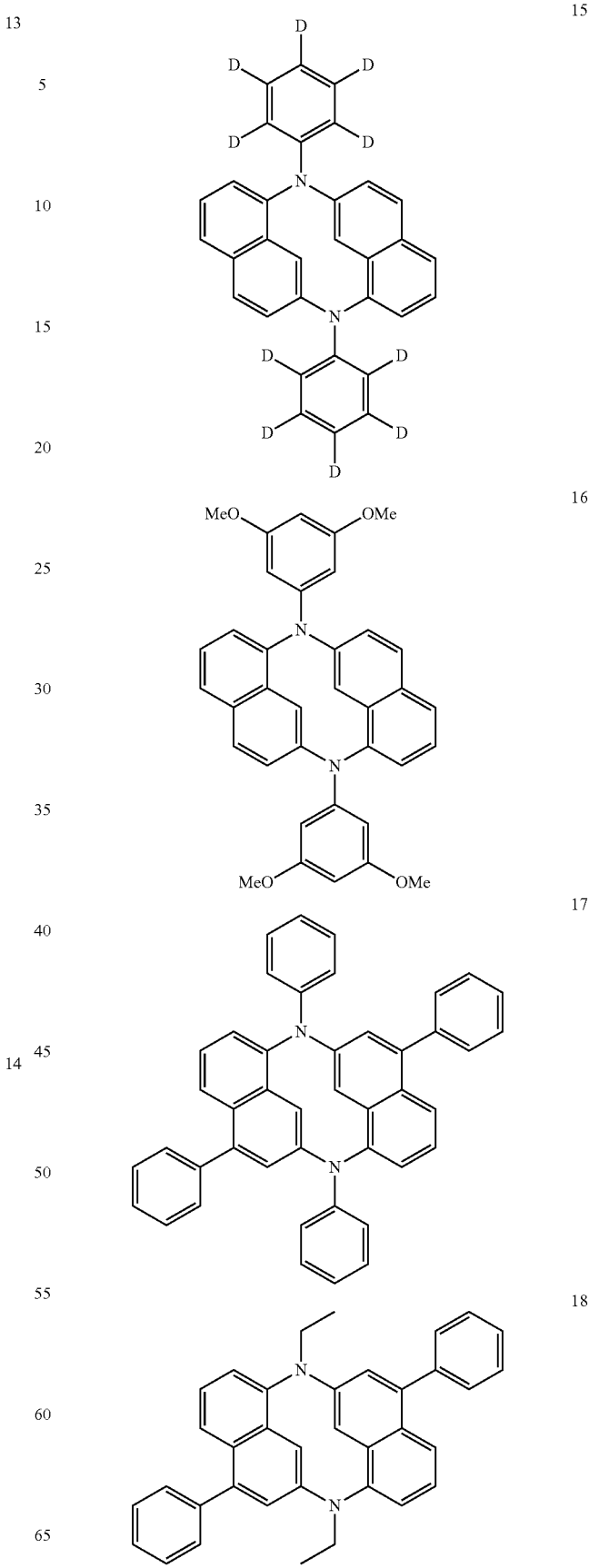

-continued
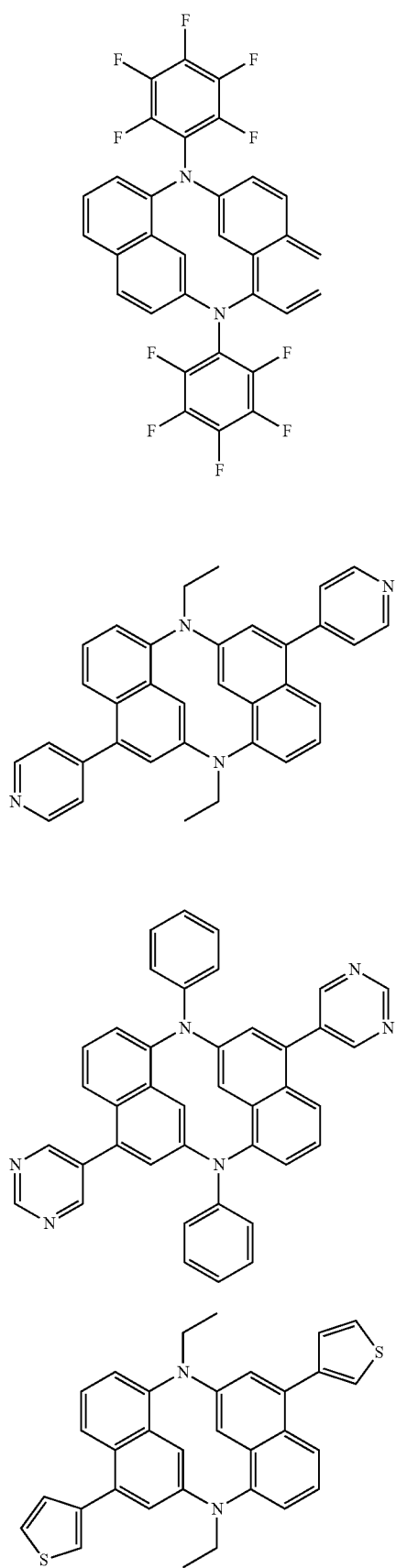
-continued
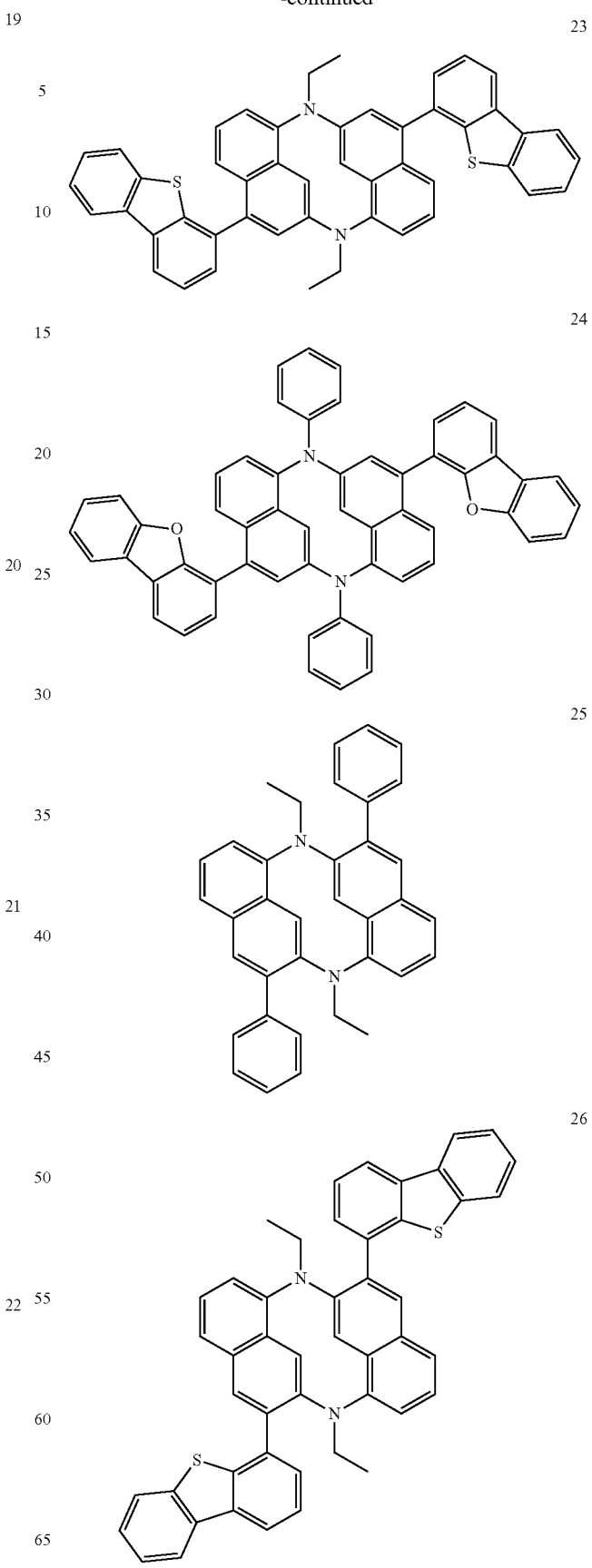

27
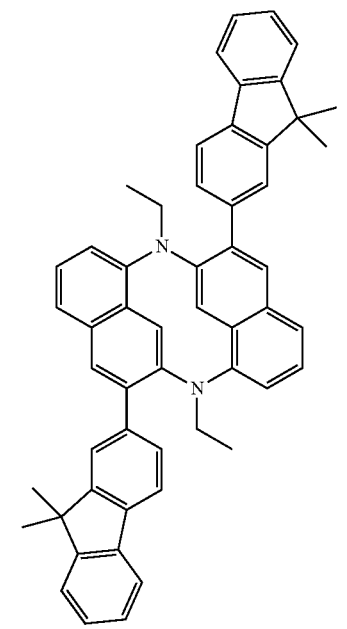
28
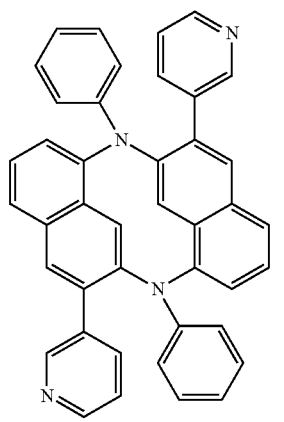
29
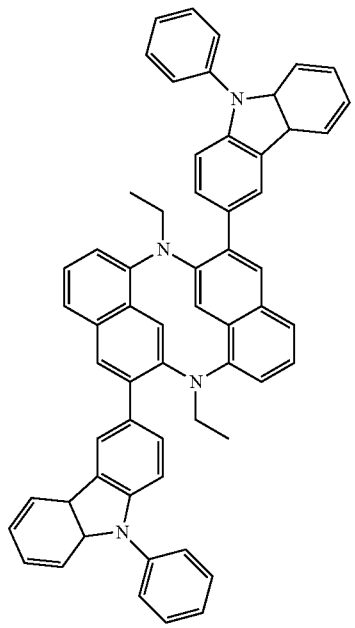
30
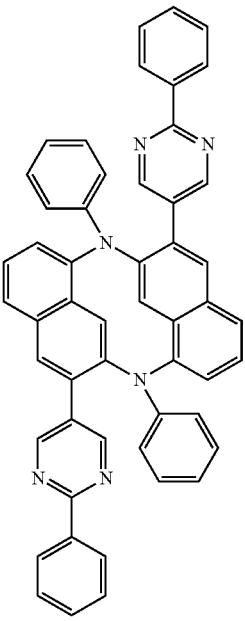
31
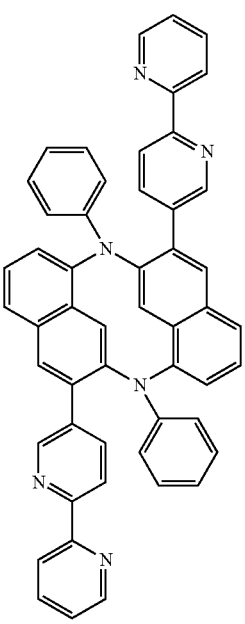
32
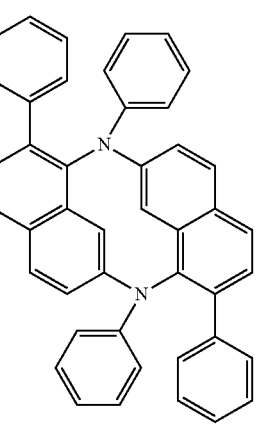

33
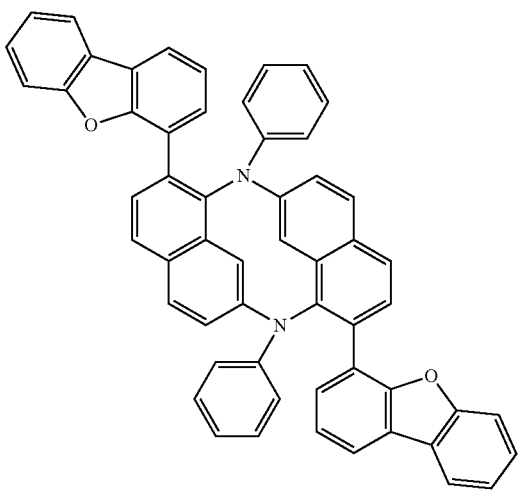
34
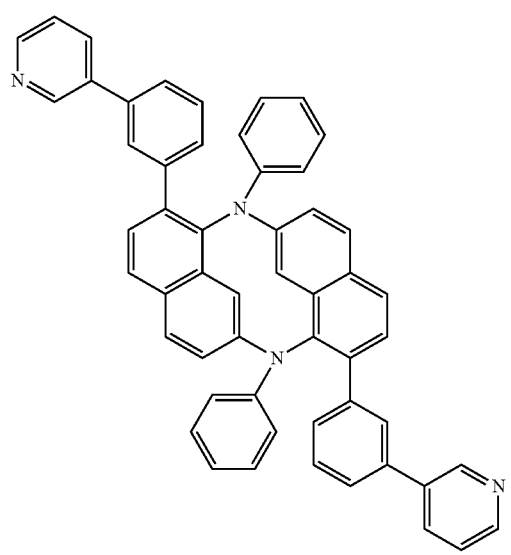
35
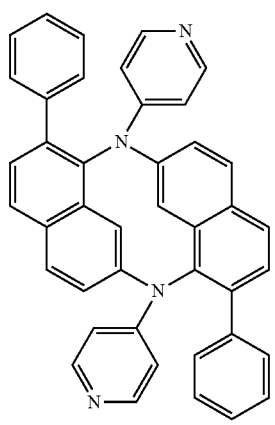
36
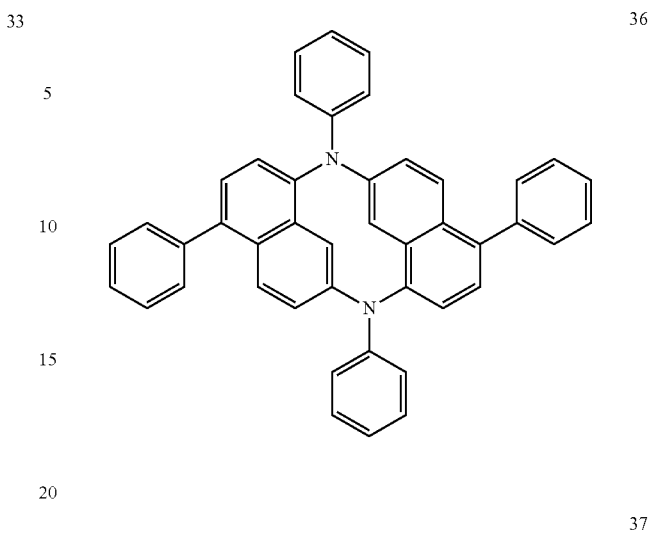
37
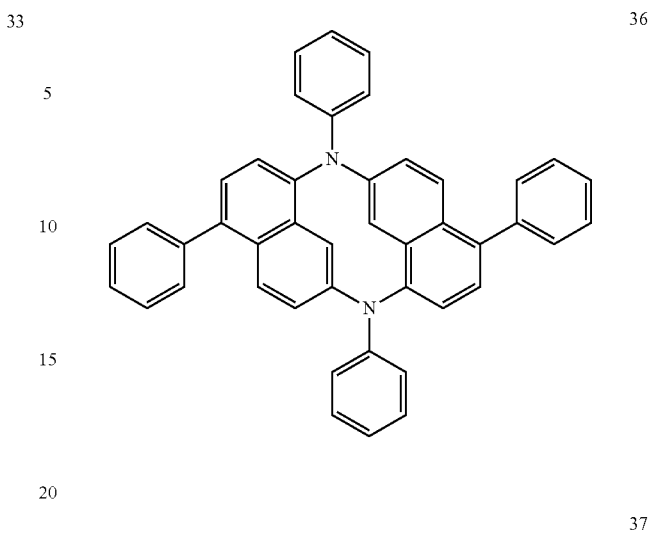
38
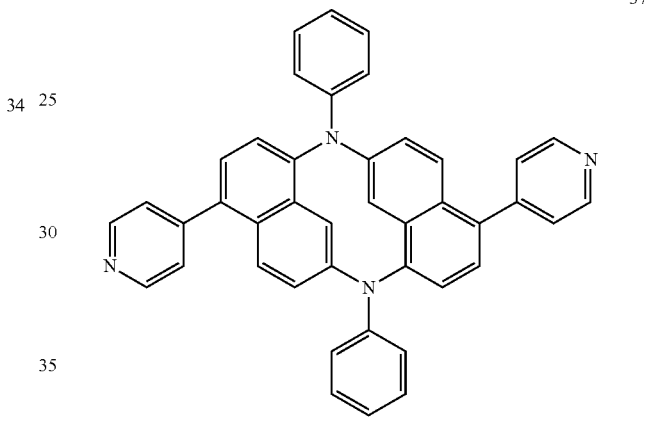
39
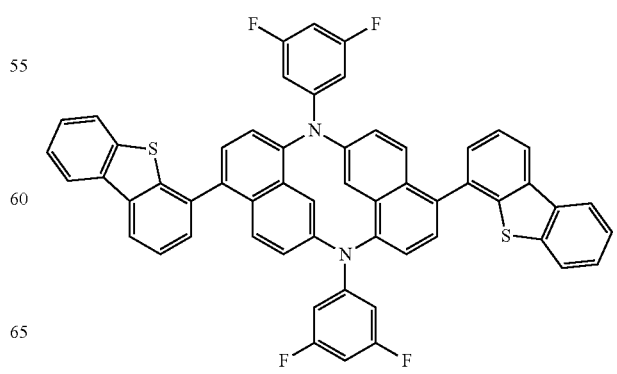

-continued
40
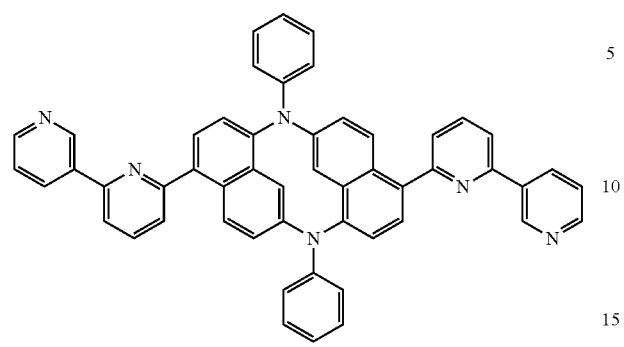
41
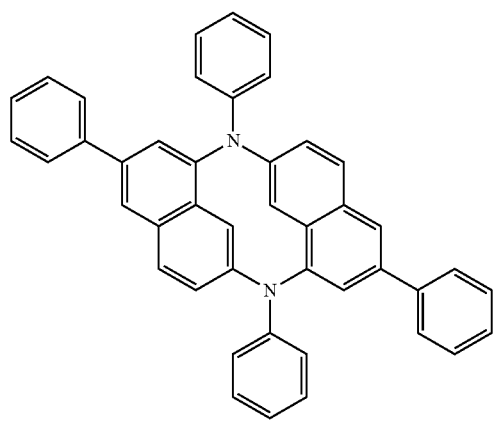
42
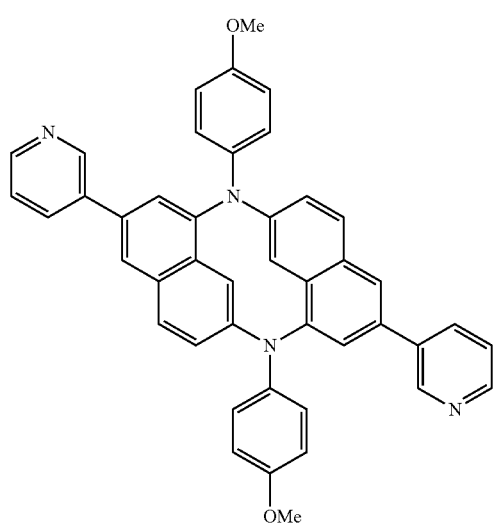
-continued
43
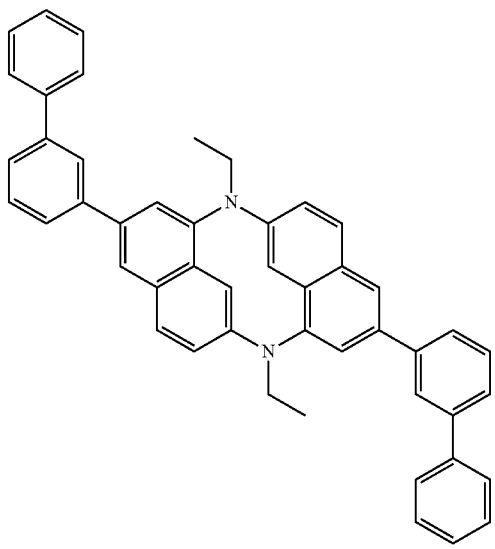
44
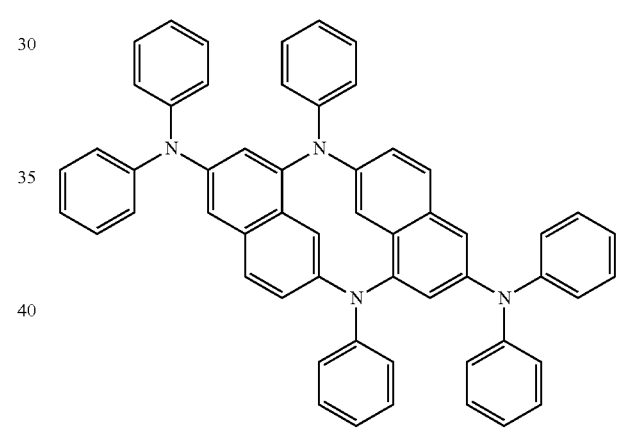
45
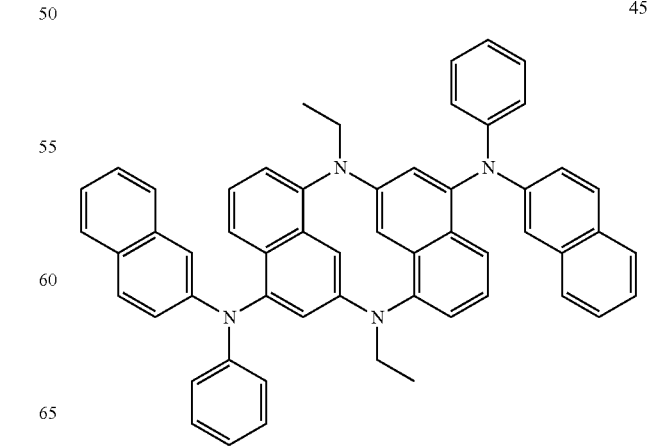

46
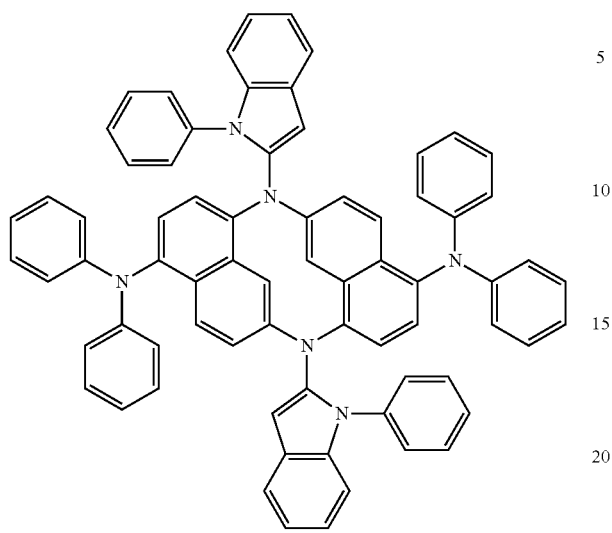
47
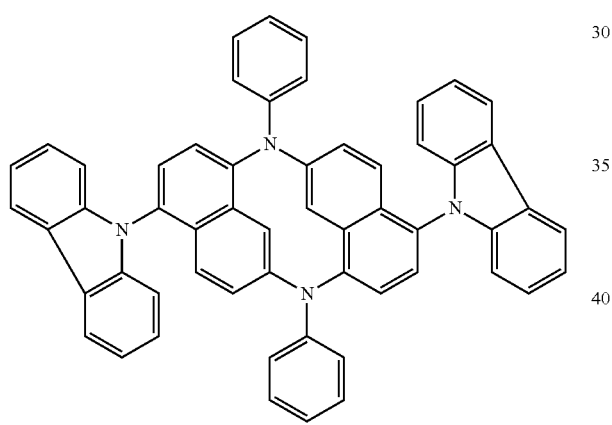
48
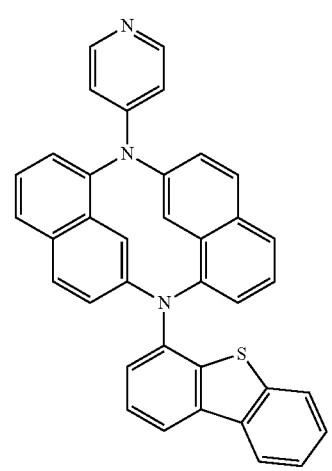
49
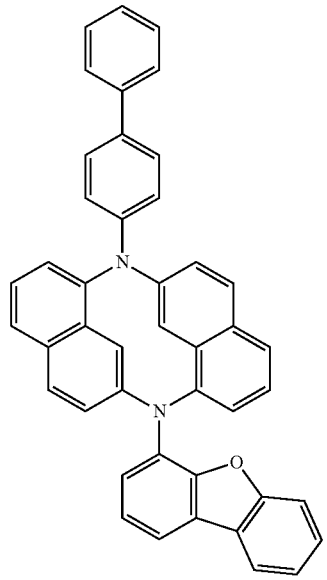
50
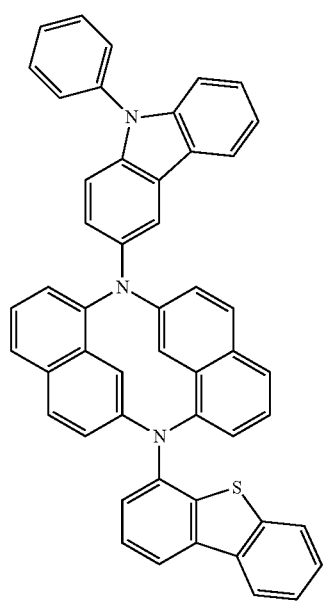
51
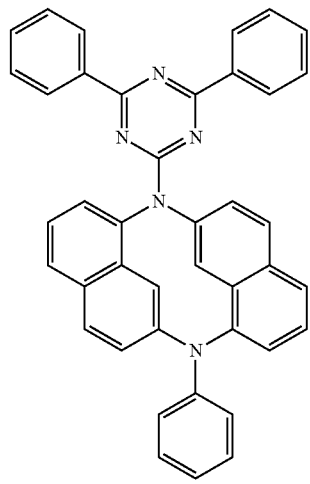

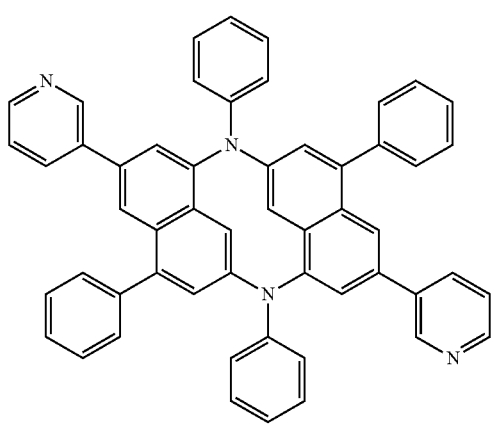
52
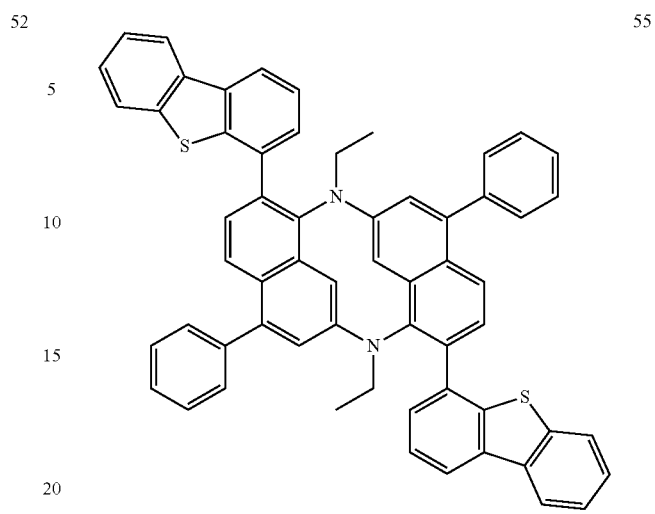
55
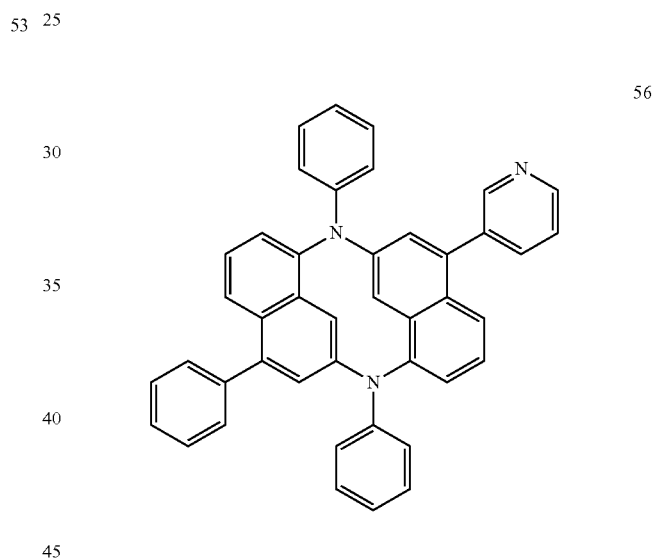
53
56
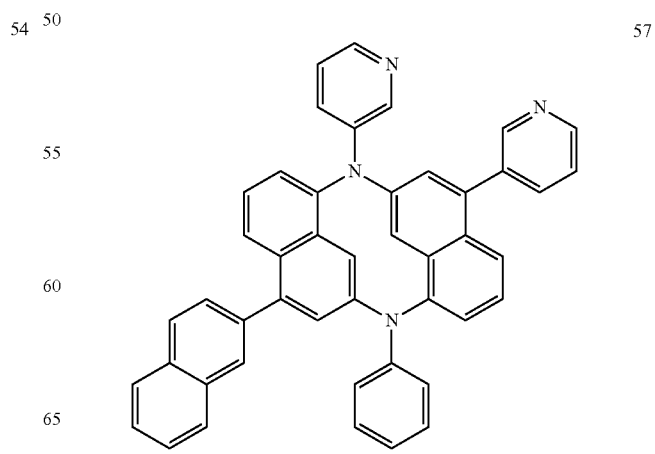
54
57

-continued
58
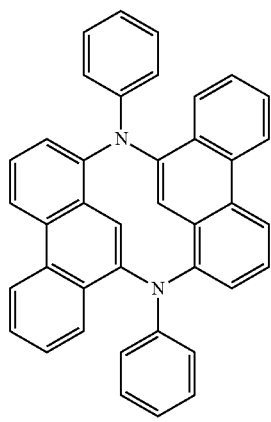
59
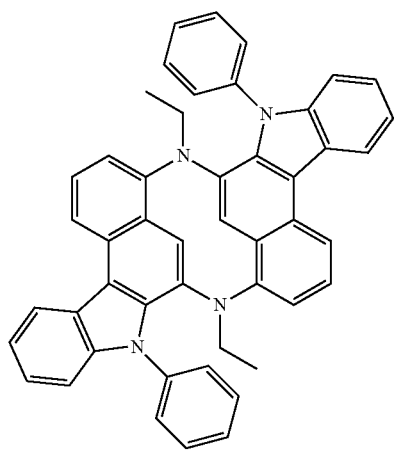
60
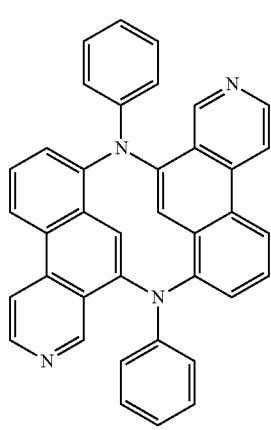
-continued
61
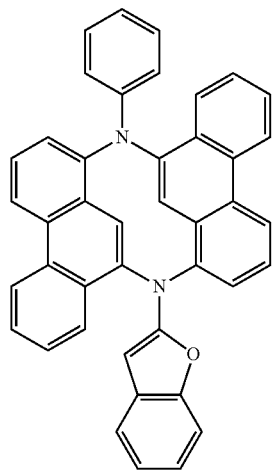
62
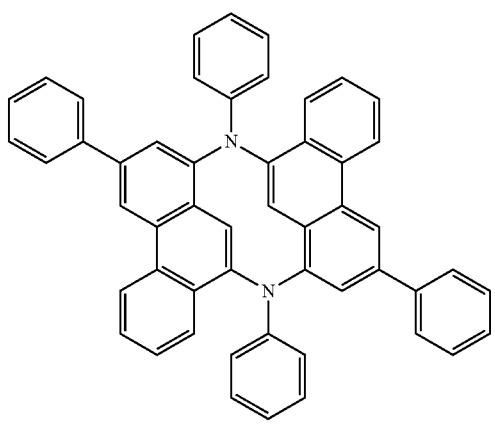
63
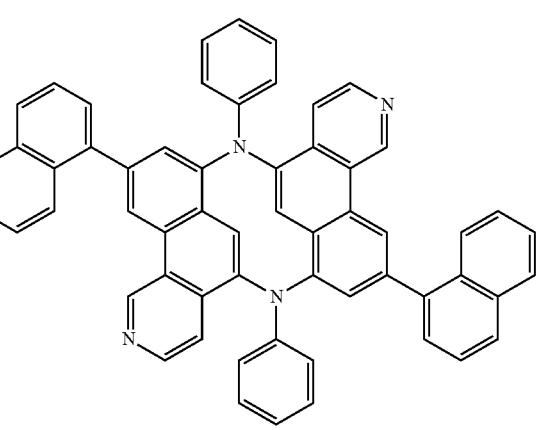

-continued
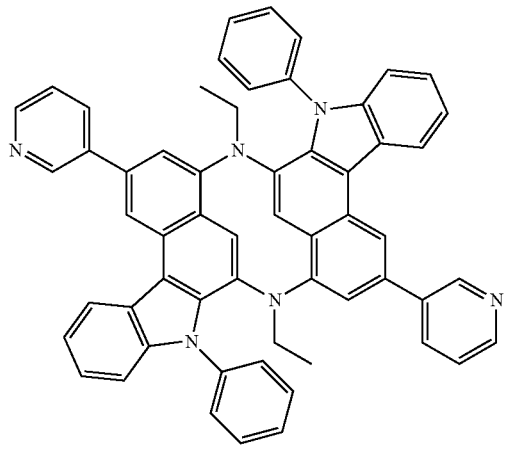
64
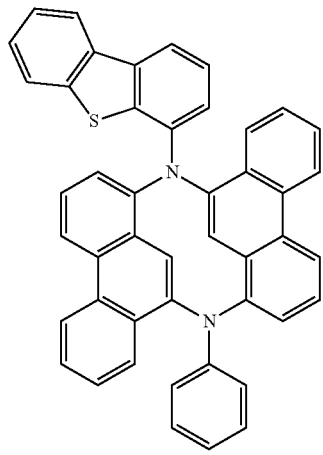
67
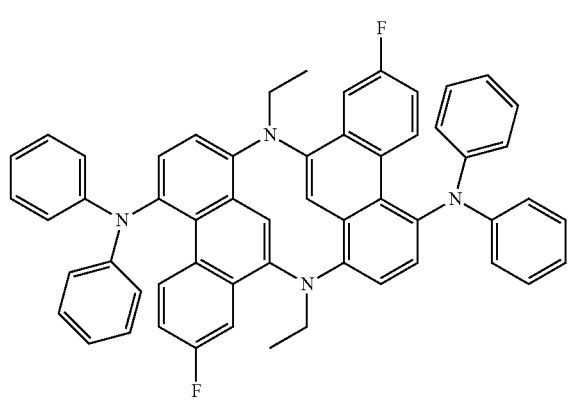
65
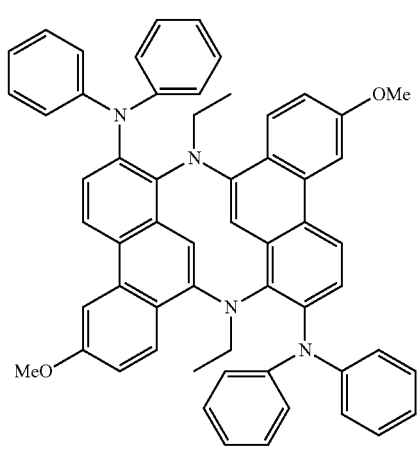
66
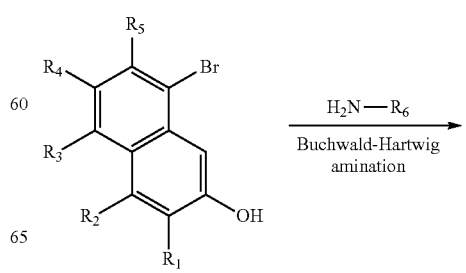
An exemplary synthesis route is shown below. The synthesizing route will be described in more detail with reference to Synthesis Examples.

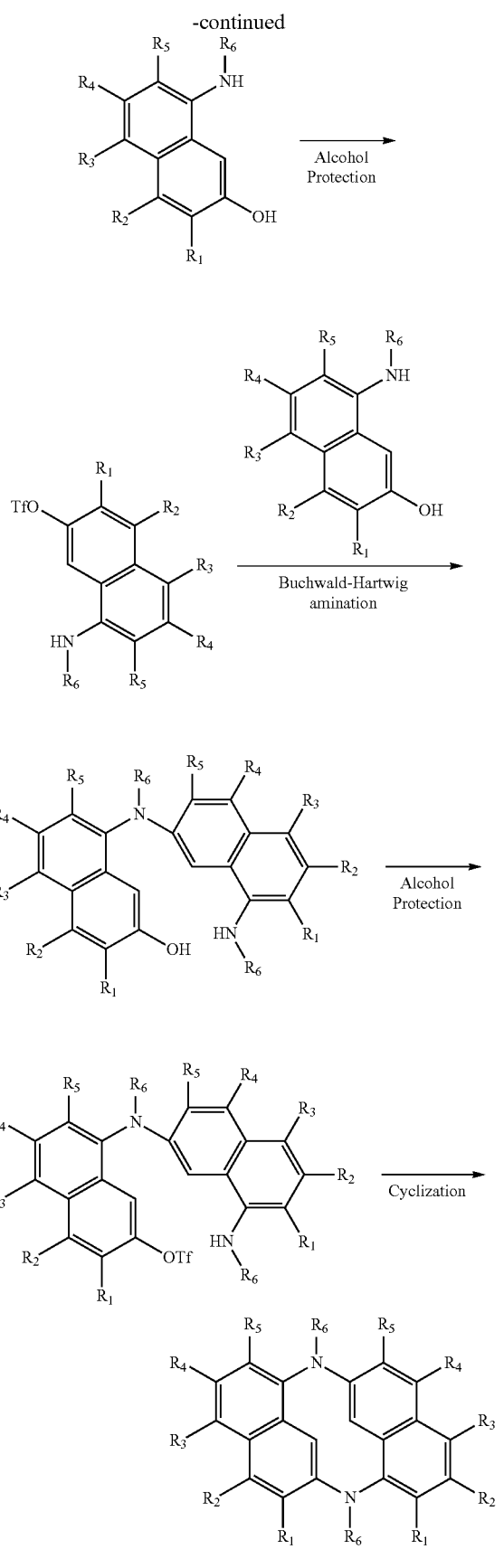
Exemplary substituents used in the above synthesis route are represented by Formulae below:
Group I
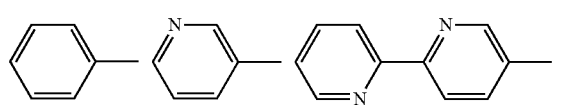
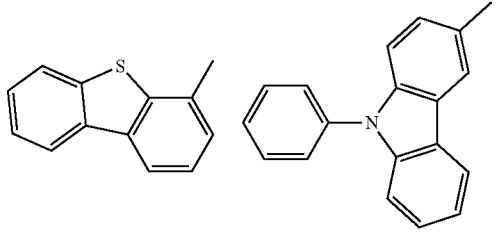
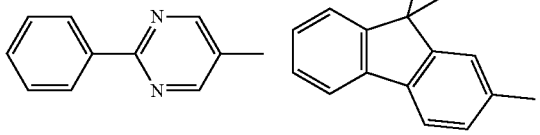
Group II
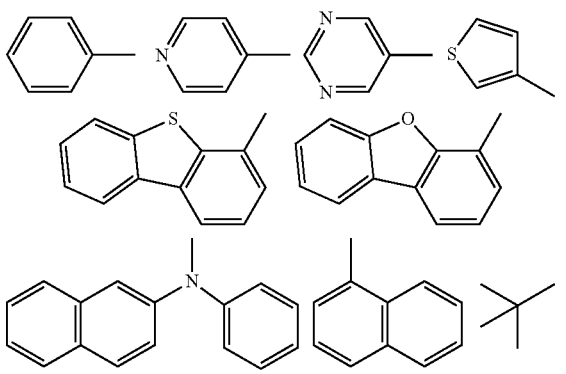
Group III
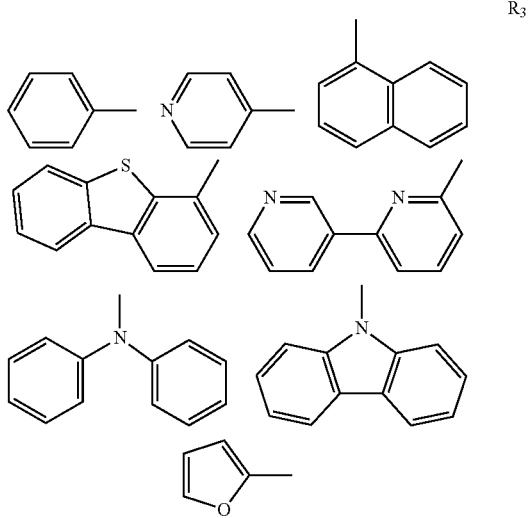
wherein Tf is $CF_3-SO_2-*$ and * indicates a binding site.

-continued

Group IV

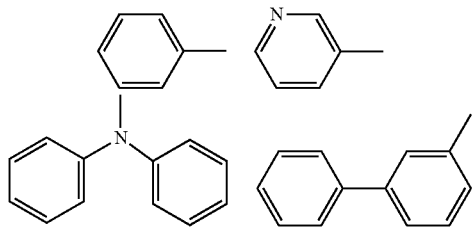

Group V

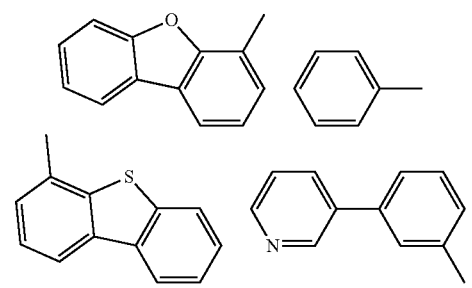

Group VI

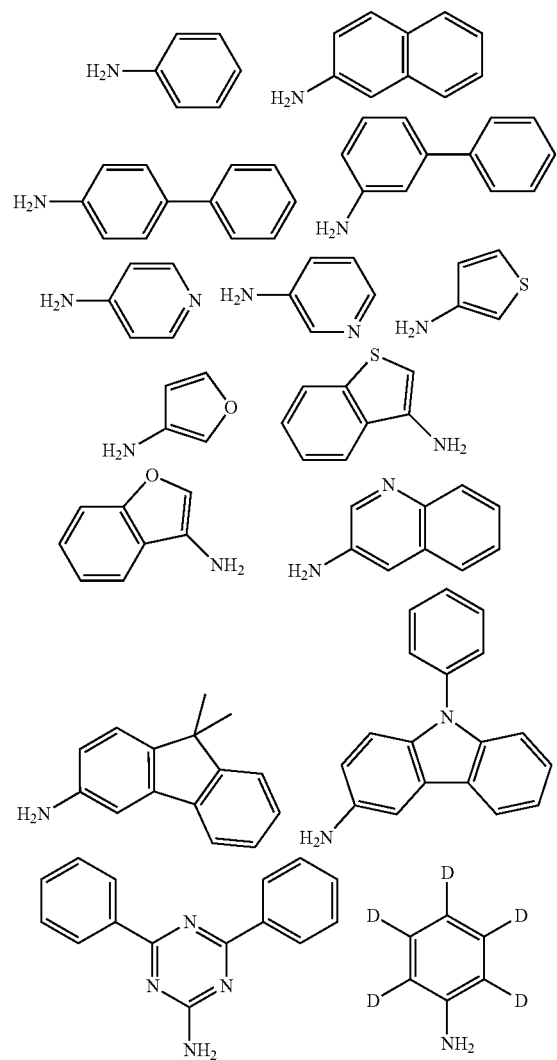

$R_4$

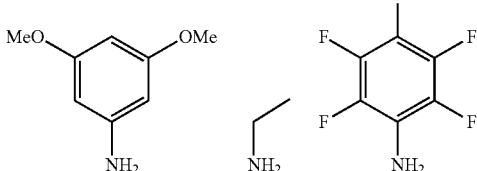

$R_5$

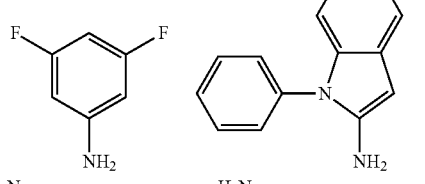

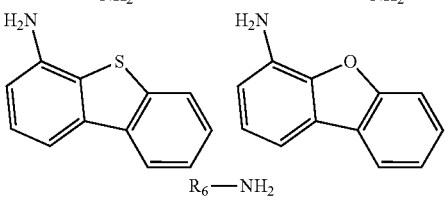

$R_6$—$NH_2$

According to an embodiment of the present invention, an organic light-emitting device includes: a first electrode; a second electrode; and an organic layer interposed between the first electrode and the second electrode, wherein the organic layer includes a first layer including the heterocyclic compound represented by Formula 1.

The first layer including the heterocyclic compound represented by Formula 1 may include a hole injection layer (HIL), a hole transport layer (HTL), a functional layer having both hole injecting and hole transporting capabilities, an EIL, an ETL, or a functional layer having both electron injecting and electron transporting capabilities.

Alternatively, the first layer may be an EML, and the heterocyclic compound of Formula 1 may be used as a host for a fluorescence or phosphorescence device.

The organic layer of the organic light-emitting device may include an EML, an HTL, and an ETL. The first layer may be the EML, and the EML may further include an anthracene compound, an arylamine compound, or a styryl compound, all of which are well known.

At least one hydrogen atom of the anthracene compound, the arylamine compound, and the styryl compound may be substituted with the same substituent groups described above with reference to the $C_1$-$C_{60}$ alkyl group. The arylamine indicates a $C_5$-$C_{60}$ arylamine group.

The organic layer of the organic light-emitting device may include an EML, an HTL, and an ETL. The first layer may be the EML, and at least one of the red, green, blue, and white layers of the EML may further include a phosphorescent compound.

The first layer of the organic light-emitting device may be a blue EML. If the organic layer of the organic light-emitting device is a blue EML, the compound of Formula 1 may be used as a blue host.

Meanwhile, the first electrode may be an anode, and the second electrode may be a cathode, but the reverse is also possible.

For example, the organic light-emitting device according to an embodiment of the present embodiment may have a structure of first electrode/HIL/EML/second electrode, a structure of first electrode/HIL/HTL/EML/ETL/second electrode, or a structure of first electrode/HIL/HTL/EML/ETL/

EIL/second electrode. The organic light-emitting device may also have a structure of first electrode/single layer having both hole injecting and hole transporting capabilities/EML/ETL/second electrode, or a structure of first electrode/single layer having both hole injecting and hole transporting capabilities/EML/ETL/EIL/second electrode. The organic light-emitting device may also have a structure of first electrode/HTL/EML/single layer having both electron injecting and electron transporting capabilities/second electrode, a structure of first electrode/HIL/EML/single layer having both electron injecting and electron transporting capabilities/second electrode, or a structure of first electrode/HIL/HTL/EML/single layer having both electron injecting and electron transporting capabilities/second electrode.

The organic light-emitting device according to an embodiment of the present embodiment may be a top-emission type organic light-emitting device or a bottom-emission type organic light-emitting device.

The organic layer of the organic light-emitting device may include a HIL, a HTL, a functional layer having both hole injecting and hole transporting capabilities, an EML, a hole blocking layer (HBL), an ETL, an EIL, or a combination of at least two thereof, but is not limited thereto. At least one of the HIL, the HTL, and the functional layer having both hole injecting and hole transporting capabilities may further include a charge-generating material in addition to the heterocyclic compound according to an embodiment of the present invention, known hole injecting materials, and known hole transporting materials, in order to improve conductivity of the layers.

The charge-generating material may be a p-dopant. Examples of the p-dopant include a quinone derivative such as tetracyanoquinonedimethane (TCNQ) and 2,3,5,6-tetrafluoro-tetracyano-1,4-benzoquinonedimethane (F4TCNQ); a metal oxide such as tungsten oxide and molybdenum oxide; and a cyano group-containing compound such as Compound 100 below, but are not limited thereto.

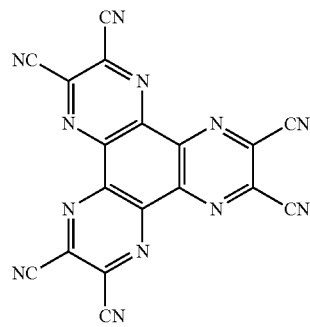

Compound 100

If the HIL, the HTL, or the functional layer having both hole injecting and hole transporting capabilities further includes the charge-generating material, the charge-generating material may be homogeneously or non-homogeneously dispersed between the layers, or a variety of modifications may be possible.

The ETL of the organic light-emitting device may include an electron-transporting organic compound and a metal-containing material. Examples of the electron-transporting compound include anthracene-based compounds such as 9,10-di(naphthalene-2-yl)anthracene) (ADN), and Compounds 101 and 102 below, but are not limited thereto.

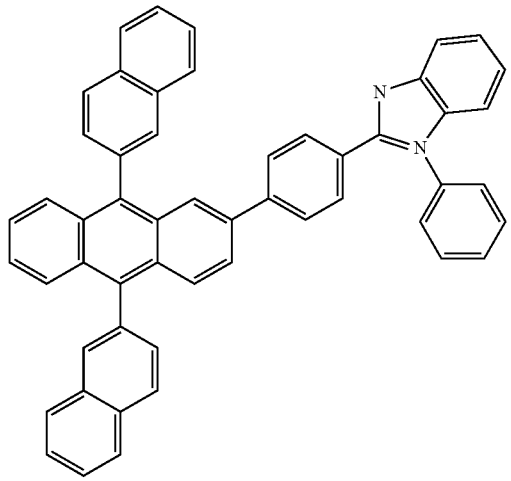

Compound 101

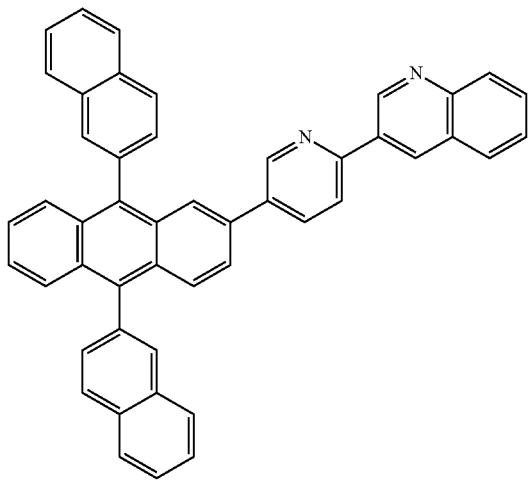

Compound 102

The metal-containing material may include a Li complex. Examples of the Li complex include lithium quinolate (LiQ) or Compound 103 below, but are not limited thereto.

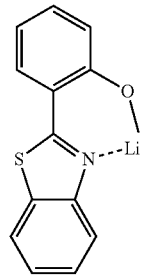

Compound 103

Hereinafter, a method of manufacturing an organic light-emitting device according to an embodiment of the present invention will be described with reference to FIG. 1. Referring to FIG. 1, the organic light-emitting device according to an embodiment of the present embodiment includes a substrate (not shown), a first electrode (anode), a HIL, a HTL, an EML, an ETL, an EIL, and a second electrode (cathode).

First, the first electrode is formed by depositing or sputtering a material for forming the first electrode having a high work function on a substrate. The first electrode may constitute an anode or a cathode. The substrate may be any substrate commonly used in organic light-emitting devices, and may include, for example, a glass substrate or a transparent plastic substrate with excellent mechanical strength, thermal stability, transparency, surface smoothness, ease of handling, and water resistance. The material for forming the first electrode may be indium tin oxide (ITO), indium zinc oxide (IZO), tin oxide ($SnO_2$), zinc oxide (ZnO), aluminum (Al), silver (Ag), magnesium (Mg), or the like, which has excellent conductivity, and may form a transparent or reflective electrode.

Then, a HIL may be formed on the first electrode by vacuum deposition, spin coating, casting, Langmuir Blodgett (LB) deposition, or the like.

When the HIL is formed using vacuum deposition, the deposition conditions may vary according to a compound that is used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of 0.01 to 100 Å/sec.

When the HIL is formed using spin coating, coating conditions may vary according to a compound that is used to form the HIL, and the structure and thermal properties of the HIL to be formed. For example, the coating conditions may include a coating speed of about 2,000 rpm to about 5,000 rpm, and a thermal treatment temperature of about 80° C. to about 200° C., wherein the thermal treatment is for removing a solvent after coating.

The HIL may be formed of the compound represented by Formula 1 or any material that is commonly used to form a HIL. Examples of the material include a phthalocyanine compound such as copperphthalocyanine, 4,4',4''-tris(3-methylphenylphenylamino) triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and (polyaniline)/poly(4-styrenesulfonate (PANI/PSS), but are not limited thereto.

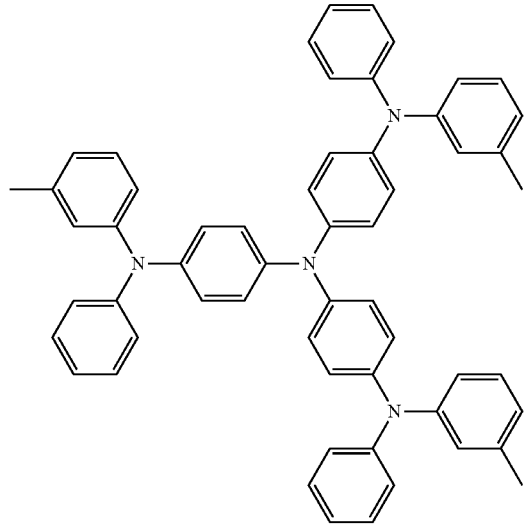

m-MTDATA

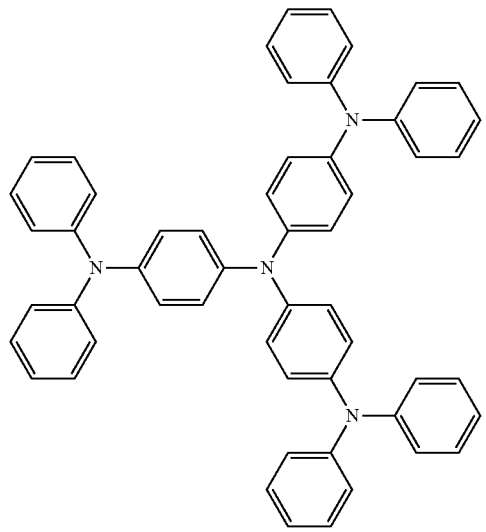

TDATA

2T-NATA

The thickness of the HIL may be about 100 to 10,000 Å, and for example, 100 to 1,000 Å. When the HIL has a thickness within the above range, the HIL may have excellent hole injection characteristics without an increase in driving voltage.

Then, the HTL may be formed on the HIL using various methods, for example by vacuum deposition, spin coating, casting, and LB deposition. When the HTL is formed using vacuum deposition or spin coating, the deposition or coating conditions may be similar to those applied to form the HIL, although the deposition or coating conditions may vary according to a material used to form the HTL.

Alternatively, the heterocyclic compound represented by Formula 1 or known HTL materials may be used as HTL materials. Examples of such HTL materials include, but are not limited to, carbazole derivatives such as N-phenylcarbazole or polyvinylcarbazole, and amine derivatives having an aromatic condensed ring, such as NPB and N,N'-bis(3-methylphenyl)-N,N'-diphenyl-[1,1-biphenyl]-4,4'-diamine (TPD).

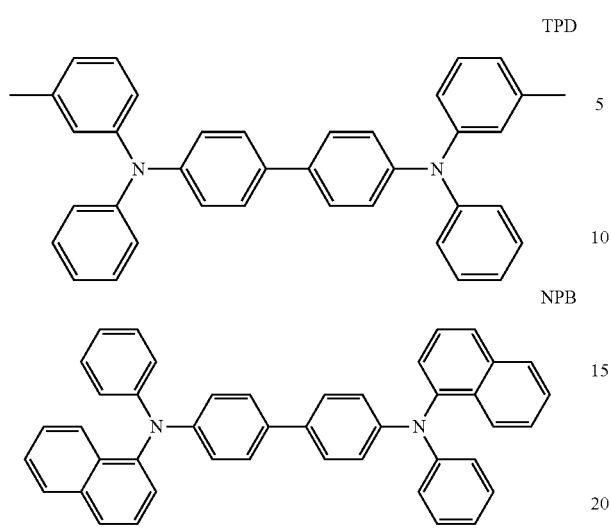

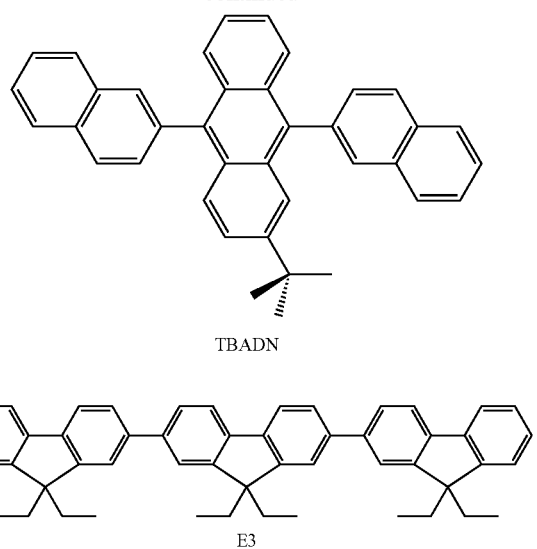

The HTL may have a thickness of about 50 Å to about 1,000 Å, for example, about 100 Å to about 600 Å. When the HTL has a thickness within the above range, the HTL may have excellent hole transporting characteristics without a substantial increase in driving voltage.

Then, the EML may be formed on the HTL using various methods, for example, vacuum deposition, spin coating, casting, and LB deposition. When the EML is formed using vacuum deposition or spin coating, the deposition or coating conditions may be similar to those applied to form the HIL, although the deposition and coating conditions may vary according to a material that is used to form the EML.

The EML may include the heterocyclic compound of Formula 1 described above. In particular, the heterocyclic compound of Formula 1 may be used as a host or a dopant. The EML may be formed using a variety of well-known light-emitting materials instead of the heterocyclic compound of Formula 1. Alternatively, the EML may also be formed using a well-known host and a dopant. The dopant for forming the EML may include either a fluorescent dopant or a phosphorescent dopant, which are widely known in the art.

Examples of the host include Alq3, 4,4'-N,N'-dicarbazole-biphenyl (CBP), poly(n-vinylcarbazole) (PVK), 9,10-di(naphthalene-2-yl)anthracene (ADN), 1,3,5-tris(N-phenyl-benzimidazole-2-yl)benzene (TPBI), 3-tert-butyl-9,10-di(naphtha-2-yl)anthracene (TBADN), E3, and distyrylarylene (DSA), bur are not limited thereto.

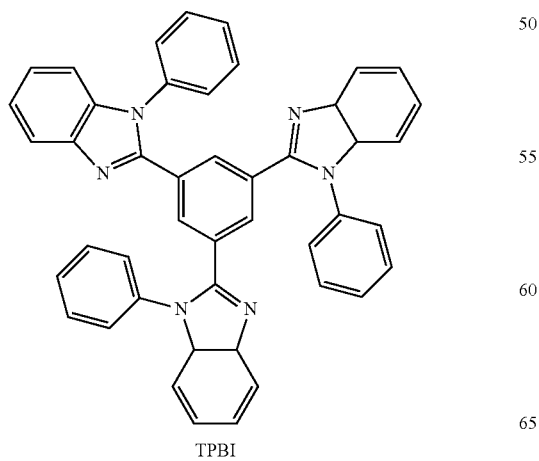

Examples of well-known red dopants include platinum(II) octaethylporphyrin (PtOEP), Ir(piq)$_3$, Btp$_2$Ir(acac), and DCJTB, but are not limited thereto.

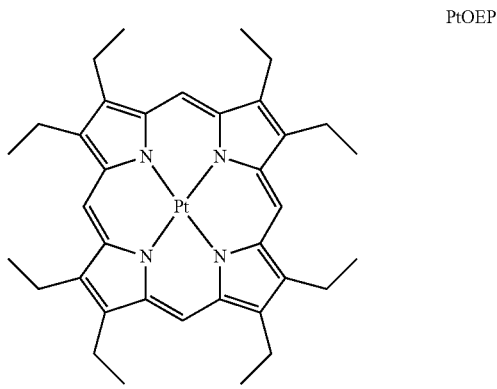

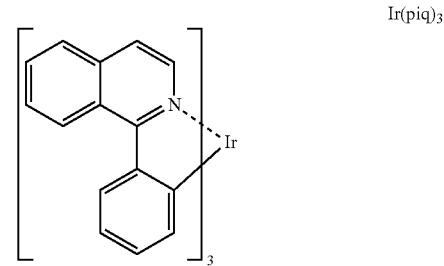

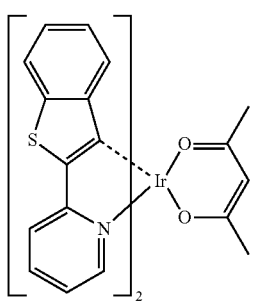

Btp₂Ir(acac)

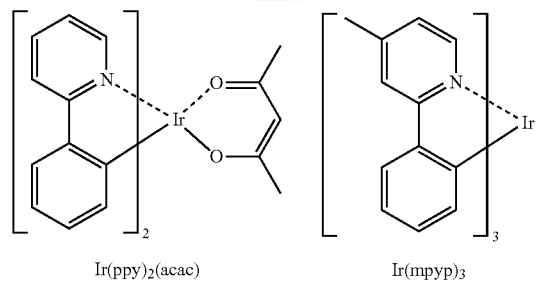

Ir(ppy)₂(acac)　　　Ir(mpyp)₃

Examples of known green dopants include Ir(ppy)₃ (where "ppy" denotes phenylpyridine), Ir(ppy)₂(acac), Ir(mpyp)₃, and C545T, but are not limited thereto.

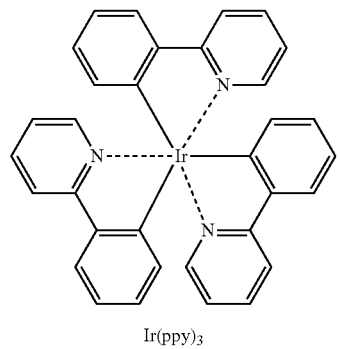

Ir(ppy)₃

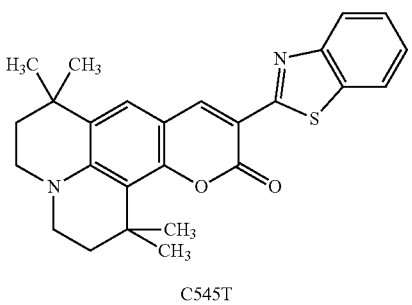

C545T

Alternatively, examples of well-known blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl phenylene (TBPe), but are not limited thereto.

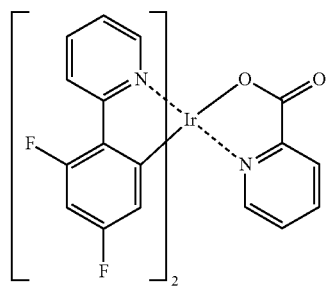

F₂Irpic

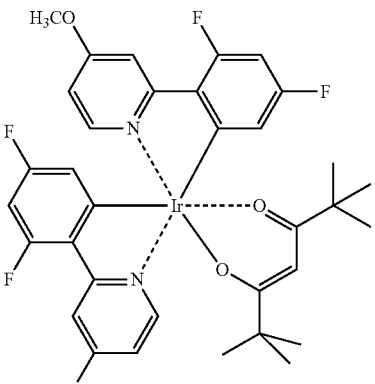

(F2ppy)2Ir(tmd)

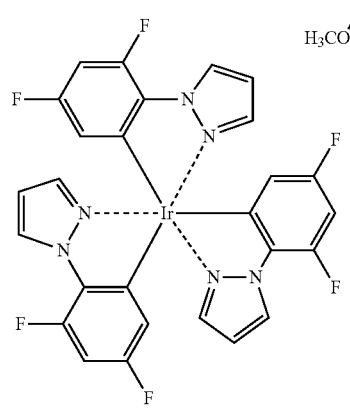

Ir(dfppz)₃

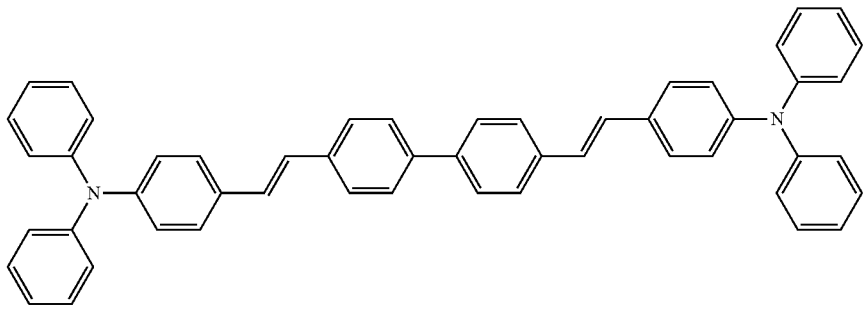
DPAVBi

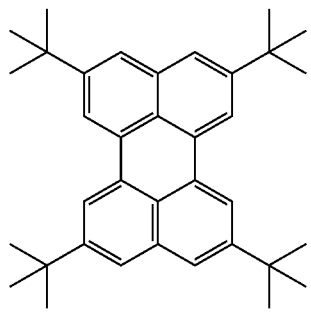
TBP

The amount of the dopant may be in a range of about 0.1 to about 20 parts by weight, for example, about 0.5 to about 12 parts by weight, based on 100 parts by weight of the EML material (which is equivalent to the total weight of the host and the dopant). When the amount of the dopant is within the above range, concentration quenching may be substantially prevented.

The EML may have a thickness of about 100 Å to about 1,000 Å, for example, about 200 Å to about 600 Å. When the EML has a thickness within the above range, the EML may have excellent light-emitting characteristics without a substantial increase in driving voltage.

When the EML includes a phosphorescent dopant, an HBL (not shown in FIG. 1) may be formed on the EML in order to prevent diffusion of triplet excitons or holes into the ETL. In this case, the HBL may be formed of any material that is commonly used to form a HBL, without limitation. Examples of such HBL materials include oxadiazole derivatives, triazole derivatives, phenanthroline derivatives, Balq, and BCP.

The HBL may have a thickness of about 50 Å to about 1,000 Å, for example, about 100 Å to about 300 Å. When the thickness of the HBL is within the range described above, the HBL may have excellent hole blocking characteristics without a substantial increase in driving voltage.

Then, the ETL is formed on the EML (or HBL) using various methods, for example, by vacuum deposition, spin coating, casting, or the like. When the ETL is formed using vacuum deposition or spin coating, the deposition or coating conditions may be similar to those applied to form the HIL, although the deposition and coating conditions may vary according to the material that is used to form the ETL.

The electron transporting material may include the heterocyclic compound of Formula 1 described above. Alternatively, the ETL may be formed of any material that is widely known in the art. Examples of electron transporting materials include quinoline derivatives, such as tris(8-quinolinolate) aluminum (Alq3), TAZ, or Balq, but are not limited thereto.

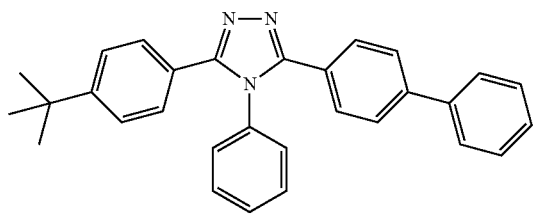
TAZ

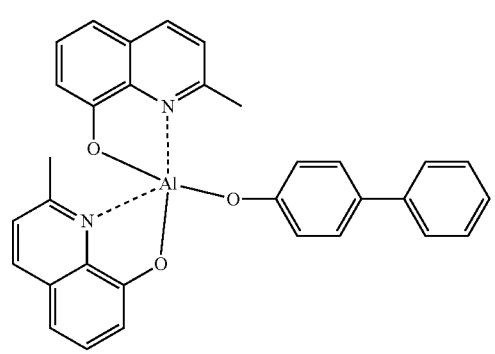
BAlq

The ETL may have a thickness of about 100 Å to about 1,000 Å, for example, about 100 Å to about 500 Å. When the ETL has a thickness within the above range, the ETL may have excellent electron transporting characteristics without a substantial increase in driving voltage.

In addition, the EIL, which facilitates injection of electrons from the cathode, may be formed on the ETL.

Alternatively, well-known materials, such as LiF, NaCl, CsF, Li$_2$O, or BaO, may be used to form the EIL. The deposition or coating conditions for forming the EIL may be similar to those applied to form the HIL, although the deposition and coating conditions may vary according to the material that is used to form the EIL.

The EIL may have a thickness of about 1 Å to 100 Å, for example, about 5 Å to about 90 Å. When the EIL has a thickness within the above range, the EIL may have excellent electron injecting characteristics without a substantial increase in driving voltage.

Finally, the second electrode may be formed on the EIL using, for example, vacuum deposition, sputtering, or the like. The second electrode may constitute a cathode or an anode. The material for forming the second electrode may include a metal, an alloy, or an electrically conductive compound which has a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like. In addition, in order to manufacture a top-emission type organic light-emitting device, a transparent cathode formed of a transparent material such as ITO or IZO may be used as the second electrode.

The organic light-emitting device according to an embodiment of the present embodiment may be included in various types of flat panel display devices, such as a passive matrix organic light-emitting display device or an active matrix organic light-emitting display device. In particular, when the organic light-emitting device is applied to an active matrix organic light-emitting display device including a thin-film transistor, the first electrode formed on the substrate may function as a pixel electrode, electrically connected to a source electrode or a drain electrode of the thin-film transistor. Moreover, the organic light-emitting device may also be applied to a flat panel display device having a double-sided screen.

According to an embodiment, an organic light-emitting device may include a plurality of organic layers, wherein at least one of the organic layers may be formed of the heterocyclic compound of Formula 1 by using a deposition method or a wet method of coating a solution of the heterocyclic compound of Formula 1.

Hereinafter, one or more embodiments will be described in detail with reference to Synthesis Examples and Examples of Compounds 1, 14, and 25. However, theses examples are not intended to limit the purpose and scope of the invention.

EXAMPLE

Reaction Scheme

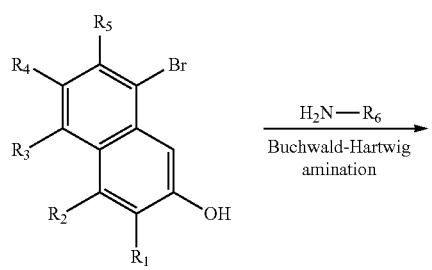

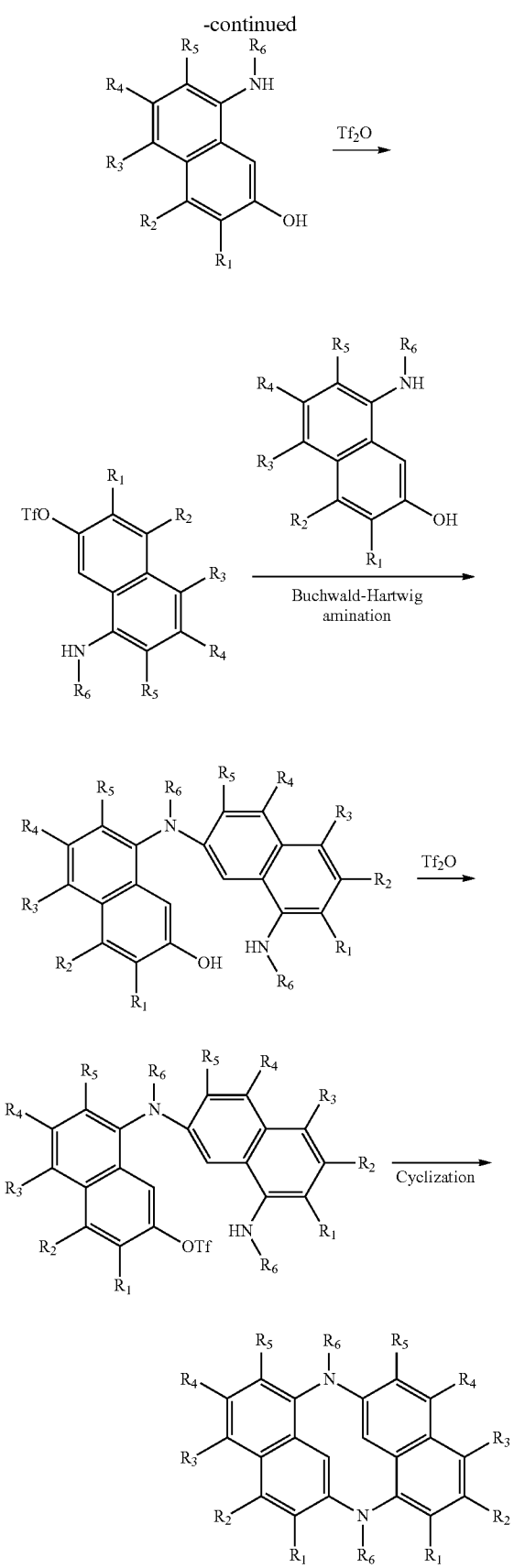

wherein Tf is $CF_3$—$SO_2$—* and * indicates a binding site.

Exemplary Synthesis Example 1

Synthesis of Compound 1

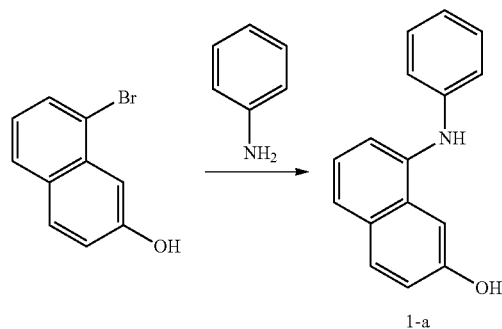

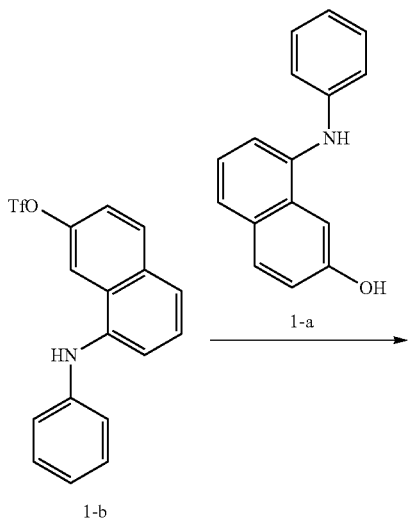

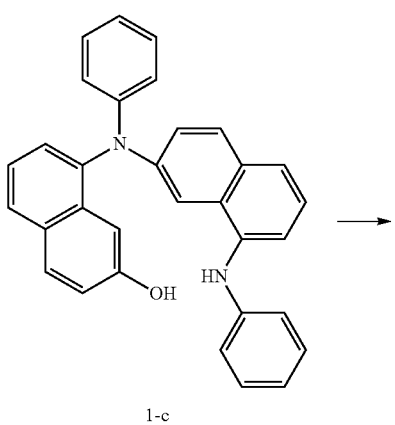

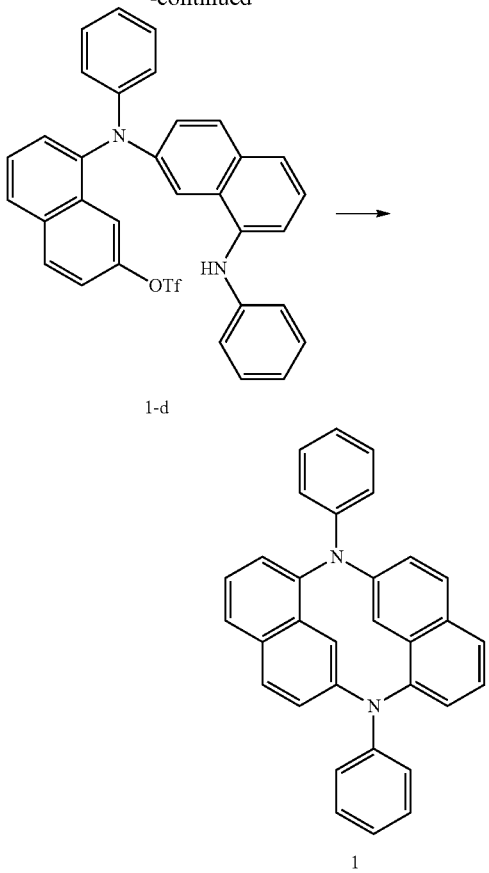

Synthesis of Intermediate 1-a 10.0 g (44.83 mmol) of 8-bromo-naphthalene-2-ol was dissolved in 100 mL of toluene. 5 g (53.79 mmol) of aniline, 6.5 g (67.24 mmol) of sodium-tert-butoxide, and 3.3 g (3.59 mmol) of tris(dibenzylideneacetone)dipalladium(0) were added thereto and were stirred for 18 hours at 120° C. After completion of the reaction, the toluene was removed by distilling the toluene with suction. 50 mL of distilled water was added thereto and then the mixture was subjected to extraction three times with each 70 mL of methylene chloride. An organic layer was collected and dried using magnesium sulfate and the solvent was evaporated. The residue was separately purified using silica gel column chromatography to obtain 9.8 g (41.65 mmol) of Intermediate 1-a (Yield: 92.9%). The produced compound was identified using LC-MS. $C_{16}H_{13}NO$: M+236.10

Synthesis of Intermediate 1-b 8.0 g (34.00 mmol) of Intermediate 1-a was dissolved in 80 mL of dichloromethane. 6.1 mL (36.26 mmol) of trifluoromethanesulfonic anhydride and 5.7 mL (40.87 mmol) of triethylamine were added thereto and were stirred for 4 hours. After completion of the reaction, 20 mL of distilled water was added thereto and the reaction was terminated. The mixture was subjected to extraction three times with each 50 mL of methylene chloride. An organic layer was collected and dried using magnesium sulfate and the solvent was evaporated. The residue was separately purified using silica gel column chromatography to obtain 11.5 g (31.31 mmol) of Intermediate 1-b (Yield 92.1%). The produced compound was identified using LC-MS. $C_{17}H_{12}F_3NO_3S$: M+368.05

Synthesis of Intermediate 1-c 9.6 g (40.80 mmol) of Intermediate 1-a and 10.0 g (27.22 mmol) of Intermediate 1-b were added to a flask and were dissolved in 100 mL of tetrahydrofuran. 7.6 mL (79.46 mmol) of N,N-diisopropyldiethylamine was added thereto and was stirred for 8 hours at room temperature. After completion of the reaction, 50 mL of distilled water was added thereto. The mixture was subjected to extraction three times with each 50 mL of methylene chloride. An organic layer was collected and dried using magnesium sulfate and the solvent was evaporated. The residue was separately purified using silica gel column chromatography to obtain 8.2 g (18.12 mmol) of Intermediate 1-c (Yield: 66.6%). The produced compound was identified using LC-MS. $C_{32}H_{24}N_2O$: M+453.19

Synthesis of Intermediate 1-d 8.0 g (17.68 mmol) of Intermediate 1-c was dissolved in 80.0 mL of dichloromethane. 3.1 mL (18.43 mmol) of trifluoromethanesulfonic anhydride and 3.0 mL (21.51 mmol) of triethylamine were added thereto and were stirred for 4 hours. After completion of the reaction, 20 mL of distilled water was added thereto and the reaction was terminated. The mixture was subjected to extraction three times with each 50 mL of methylene chloride. An organic layer was collected and dried using magnesium sulfate and the solvent was evaporated. The residue was separately purified using silica gel column chromatography to obtain 5.3 g (9.07 mmol) of Intermediate 1-d (Yield: 51.3%). The produced compound was identified using LC-MS. $C_{33}H_{23}F_3N_2O_3S$: M+585.14

Synthesis of Compound 1

5.0 g (8.55 mmol) of Intermediate 1-d was diluted in 500 mL (molar ratio of 0.02) of tetrahydrofuran and was stirred for 18 hours at 90° C. After completion of the reaction, the solvent was evaporated. The residue was separately purified using silica gel column chromatography to obtain 1.5 g (3.45 mmol) of Compound 1 (Yield: 40.3%). The produced compound was identified using LC-MS. $C_{32}H_{22}N_2$: M+435.18

Synthesis Example 2

Synthesis of Compound 14

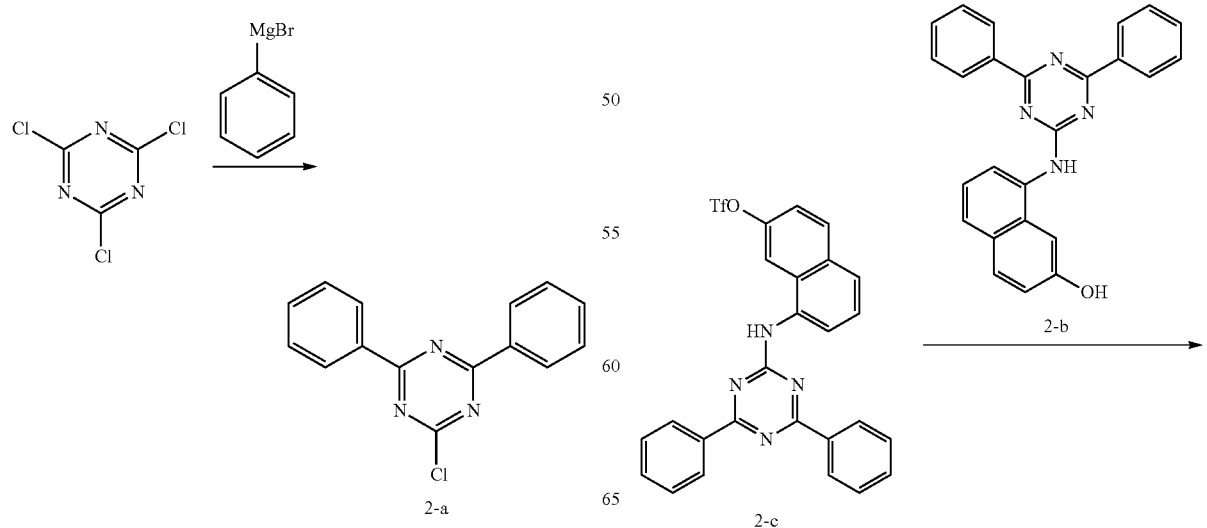

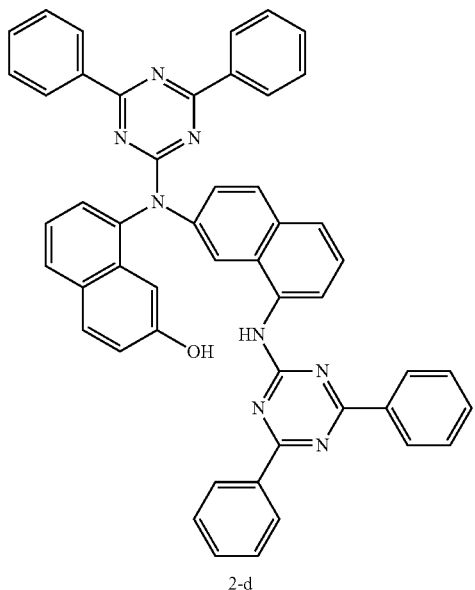

2-d

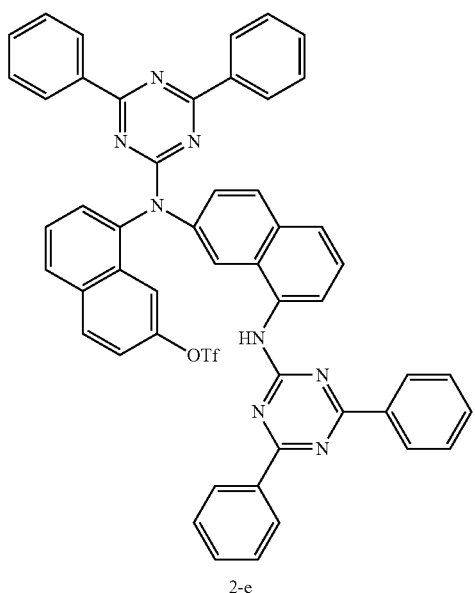

2-e

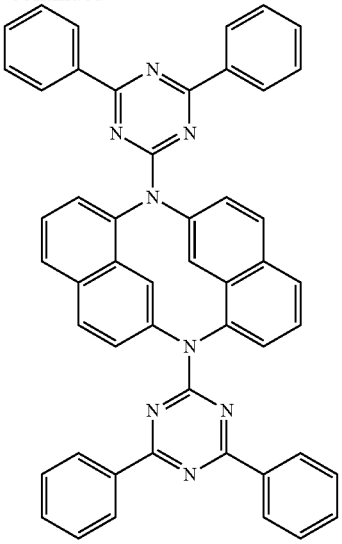

14

Synthesis of Intermediate 2-a 10.0 g (54.22 mmol) of cyanuric chloride was dissolved in 35 mL of THF and was cooled to 0° C. 45.1 mL (135.56 mmol) of phenylmagnesium bromide (3.0 M in diethylether) was slowly added thereto and was stirred for 3 hours at room temperature. In this case, the produce solid was filtered with suction and was washed by methanol and n-hexane. 9.0 g (33.62 mmol) of Compound 2-a (Yield: 62.0%) was obtained. The produced compound was identified using LC-MS. $C_{15}H_{10}ClN_3$: M+268.06

Synthesis of Intermediate 2-b 10.0 g (62.82 mmol) of 8-amino-2-naphthol was dissolved in 100 mL of toluene. 20.2 g (75.38 mmol) of Intermediate 2-a, 9.1 g (94.23 mmol) of sodium-tert-butoxide, and 4.6 g (5.03 mmol) of tris(dibenzylideneacetone)dipalladium(0) were added thereto and were stirred for 18 hours at 120° C. After completion of the reaction, the toluene was removed by distilling the toluene with suction. 50 mL of distilled water was added thereto and then the mixture was subjected to extraction three times with each 70 mL of methylene chloride. An organic layer was collected and dried using magnesium sulfate and the solvent was evaporated. The residue was separately purified using silica gel column chromatography to obtain 24.8 g (57.1 mmol) of Intermediate 2-b (Yield: 90.9%). The produced compound was identified using LC-MS. $C_{25}H_{18}N_4O$: M+390.15

Synthesis of Intermediate 2-c 12.0 g (27.62 mmol) of Intermediate 2-b was dissolved in 80 mL of dichloromethane. 5.4 mL (32.27 mmol) of trifluoromethanesulfonic anhydride) and 5.1 mL (36.88 mmol) of triethylamine were added thereto and were stirred for 4 hours. After completion of the reaction, 20 mL of distilled water was added thereto and the reaction was terminated. The mixture was subjected to extraction three times with each 50 mL of methylene chloride. An organic layer was collected and dried using magnesium sulfate and the solvent was evaporated. The residue was separately purified using silica gel column chromatography to obtain 14.2 g (27.18 mmol of Intermediate 2-c (Yield: 88.4%). The produced compound was identified using LC-MS. $C_{26}H_{17}F_3N_4O_3S$: M+523.10

Synthesis of Intermediate 2-d 10.0 g (19.14 mmol) of Intermediate 2-c and 11.2 g (28.71 mmol) of Intermediate 2-b were added to a flask and were dissolved in 100 mL of tetrahydrofuran. 10.0 mL (57.42 mmol) of N,N-diisopropyldiethylamine was added thereto and was stirred for 8 hours at room temperature. After completion of the reaction, 50 mL of distilled water. The mixture was subjected to extraction three times with each 50 mL of methylene chloride. An organic layer was collected and dried using magnesium sulfate and the solvent was evaporated. The residue was separately purified using silica gel column chromatography to obtain 9.4 g (12.35 mmol of Intermediate 2-d (Yield: 64.5%). The produced compound was identified using LC-MS. $C_{50}H_{34}N_8O$: M+763.29

Synthesis of Intermediate 2-e 8.0 g (10.49 mmol) of Intermediate 2-d was dissolved in 80.0 mL of dichloromethane. 1.9 mL (11.0 mmol) of trifluoromethanesulfonic anhydride and 1.76 mL (12.58 mmol) of triethylamine were added thereto and were stirred for 4 hours. After completion of the reaction, 20 mL of distilled water was added thereto and the reaction was terminated. The mixture was subjected to extraction three times with each 50 mL of methylene chloride. An organic layer was collected and dried using magnesium sulfate and the solvent was evaporated. The residue was separately purified using silica gel column chromatography to obtain 4.9 g (5.48 mmol) of Intermediate 2-e (Yield: 52.2%). The produced compound was identified using LC-MS. $C_{51}H_{33}F_3N_8O_3S$: M+895.23

Synthesis of Compound 14

4.0 g (4.47 mmol) of Intermediate 2-e was diluted in 230 mL (0.02 M) of tetrahydrofuran and was stirred for 18 hours at 90° C. After completion of the reaction, the solvent was evaporated. The residue was separately purified using silica gel column chromatography to obtain 1.4 g (1.84 mmol) of Compound 14 (Yield: 41.2%). The produced compound was identified using LC-MS. $C_{50}H_{32}N_8$: M+745.27

Synthesis Example 3

Synthesis of Compound 25

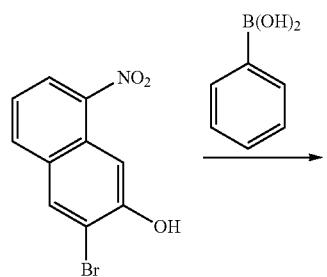

3-a

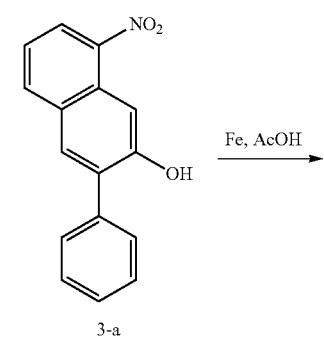

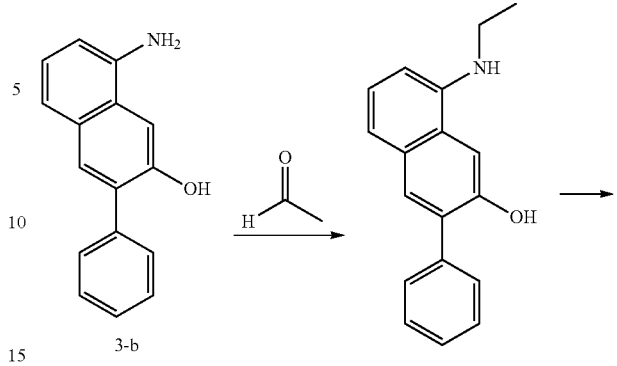

3-b → 3-c

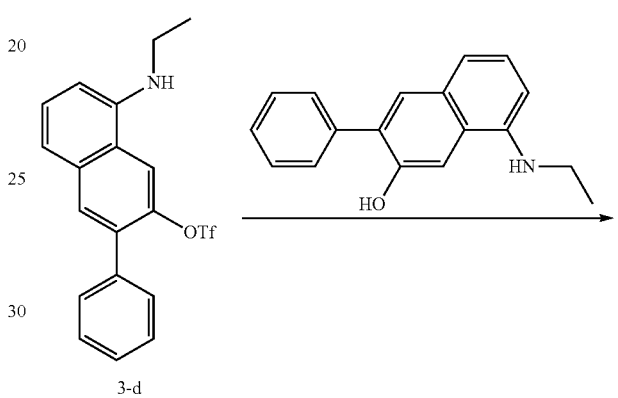

3-d

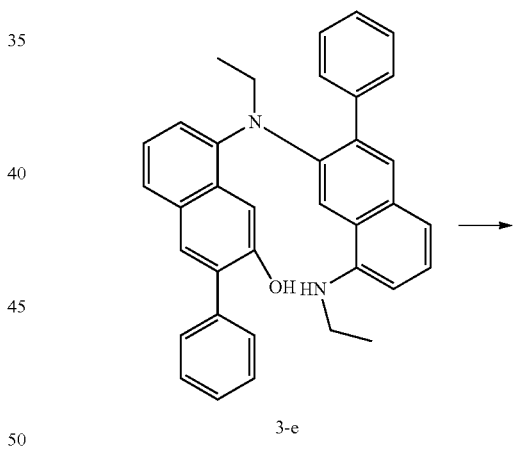

3-e

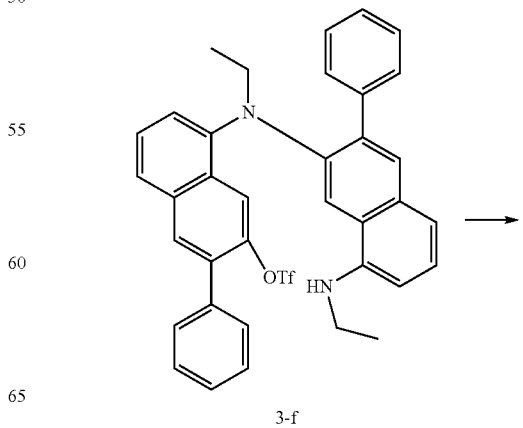

3-f

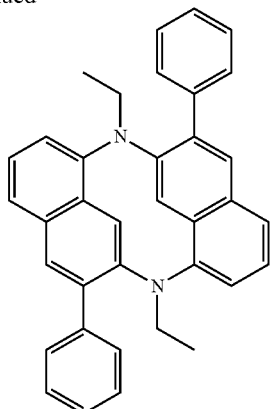

Synthesis of Intermediate 3-a 10.0 g (37.31 mmol) of 3-bromo-8-nitro-naphthalene-2-ol and 20.2 g (75.39 mmol) of phenylbornic acid were dissolved in 120 mL of toluene. 9.1 g (94.23 mmol) of $K_2CO_3$, and 4.6 g (5.03 mmol) of Pd $(PPh_3)_4$ were added thereto and were stirred for 18 hours at 120° C. After completion of the reaction, 50 mL of distilled water was added thereto and the reaction was terminated. The mixture was subjected to extraction three times with each 70 mL of methylene chloride. An organic layer was collected and washed three times by 50 mL of saturated sodium chloride (sat. NaCl) aqueous solution. An organic layer was collected and dried using magnesium sulfate and the solvent was evaporated. The residue was separately purified using silica gel column chromatography to obtain 8.1 g (30.57 mmol) of Intermediate 3-a (Yield: 82.0%). The produced compound was identified using LC-MS. $C_{16}H_{11}NO_3$: M+266.07

Synthesis of Intermediate 3-b 2.0 g (36.19 mmol) of iron (Fe) was mixed with 50 mL of ethanol in a glass flask. 2.6 mL (45.24 mmol) of acetic acid was added thereto and was stirred for one hour at 100° C. to activate the Fe. 8 g (30.16 mmol) of Intermediate 3-a was dissolved 20 mL of ethanol, was added to the activated Fe solution, and was stirred for two hours at 100° C. After completion of the reaction, the mixture was cooled to room temperature and an aspirator including 30 g of celite was installed. The cooled reaction solution was filtered with the aspirator. Then celite was washed three times by each 80 mL of methylene chloride. An organic layer was collected and washed two times by each 50 mL of saturated sodium hydrogen carbonate aqueous solution. The organic layer was dried using magnesium sulfate and the solvent was evaporated. The residue was washed by 50 mL of diethyl ether. 7 g (29.75 mmol) of Compound 3-b (Yield: 98.7%) was obtained. The produced compound was identified using LC-MS. $C_{16}H_{13}NO$: M+236.11

Synthesis of Intermediate 3-c

At room temperature, 7 g (29.75 mmol) of Intermediate 3-b was sufficiently dissolved in 70 mL of THF. 2.0 mL (35.70 mmol) of acetaldehyde, 9.5 g (44.63 mmol) of $NaBH(OAc)_3$, and 0.9 mL (14.88 mmol) of AcOH were added in the sequence of the stated above thereto and were stirred for 24 hours at room temperature. After the reaction completion, 20 mL of saturated sodium hydrogen carbonate aqueous solution was added thereto and the reaction was terminated. The mixture was subjected to extraction three times with each 70 mL of methylene chloride. An organic layer was collected and was washed one time by 50 mL of saturated sodium chloride (sat. NaCl) aqueous solution. The residue was dried using magnesium sulfate and the solvent was evaporated. The residue was separately purified using silica gel column chromatography to obtain 6.5 g (24.68 mmol) of Intermediate 3-c (Yield: 83.0%). The produced compound was identified using LC-MS. $C_{18}H_{17}NO$: M+264.13

Synthesis of Intermediate 3-d 10.0 g (37.98 mmol) of Intermediate 3-c was dissolved in 90 mL of dichloromethane. 6.7 mL (39.87 mmol) of trifluoromethanesulfonic anhydride and 6.4 mL (45.57 mmol) of triethylamine were added thereto and were stirred for 4 hours. After completion of the reaction, 20 mL of distilled water was added thereto and the reaction was terminated. The mixture was subjected to extraction three times with each 50 mL of methylene chloride. An organic layer was collected and dried using magnesium sulfate and the solvent was evaporated. The residue was separately purified using silica gel column chromatography to obtain 12.3 g (31.11 mmol of Intermediate 3-d (Yield: 81.9%). The produced compound was identified using LC-MS. $C_{19}H_{16}F_3NO_3S$: M+396.08

Synthesis of Intermediate 3-e 10.0 g (25.29 mmol) of Intermediate 3-d and 10.0 g (37.94 mmol) of Intermediate 3-c were added to a flask and were dissolved in 120 mL of tetrahydrofuran. 13.2 mL (75.87 mmol) of N,N-diisopropyldiethylamine was added thereto and was stirred for 8 hours at room temperature. After completion of the reaction, 40 mL of distilled water was added thereto. The mixture was subjected to extraction three times with each 80 mL of methylene chloride. An organic layer was collected and dried using magnesium sulfate and the solvent was evaporated. The residue was separately purified using silica gel column chromatography to obtain 10.9 g (14.29 mmol) of Intermediate 3-e (Yield: 56.5%). The produced compound was identified using LC-MS. $C_{36}H_{32}N_2O$: M+509.25

Synthesis of Intermediate 3-f 7.0 g (13.76 mmol) of Intermediate 3-e was dissolved in 70.0 mL of dichloromethane. 2.4 mL (14.45 mmol) of trifluoromethanesulfonic anhydride and 2.3 mL (16.51 mmol) of triethylamine were added thereto and were stirred for 4 hours. After completion of the reaction, 20 mL of distilled water was added thereto and the reaction was terminated. The mixture was subjected to extraction three times with each 50 mL of methylene chloride. An organic layer was collected and dried using magnesium sulfate and the solvent was evaporated. The residue was separately purified using silica gel column chromatography to obtain 5.2 g (8.12 mmol) of Intermediate 3-f (Yield: 59.0%). The produced compound was identified using LC-MS. $C_{37}H_{31}F_3N_2O_3S$: M+641.20

Synthesis of Compound 25

5.0 g (7.80 mmol) of Intermediate 3-f was diluted in 390 mL of (0.02 M) of tetrahydrofuran and was stirred for 18 hours at 90° C. After completion of the reaction, the solvent was evaporated. The residue was separately purified using silica gel column chromatography to obtain 1.5 g (3.06 mmol) of Compound 25 (Yield: 39.2%). The produced compound was identified using LC-MS. $C_{36}H_{30}N_2$: M+491.24

Other Compounds were synthesized in the same manner as in Synthesis Examples using the same equivalent weights and the substituents of Groups I to VI.

LC-MS and NMR data of the compounds are shown in Table below.

| Compound Number | LC-MS | ¹H NMR (CD$_2$Cl$_2$, 300 MHz) |
|---|---|---|
| 1 | C$_{32}$H$_{22}$N$_2$ M + 435.18 | δ = □7.41 (d, 2H, J = 7.31), 7.58~7.60 (m, 4H), 7.84 (d, 2H, J = 7.82), 7.86~7.89(m, 6H), 7.97 (dd, 2H, J = 8.02), 8.03 (dd, 2H, J = 8.39), 8.34 (dd, 2H, J = 2.61) |
| 2 | C$_{40}$H$_{26}$N$_2$ M + 534.21 | δ = 7.44 (d, 1H, J = 8.25), 7.56 (d, 1H, J = 8.02), 7.58 (dd, 2H, J = 8.25), 7.70 (dd, 2H, J = 9.38), 7.92 (dd, 2H, J = 2.46), 7.94 (d, 1H, J = 8.02), 7.96 (d, 1H, J = 2.53), 8.01~8.06 (m, 6H), 8.12 (dd, 2H, J = 8.37), 8.17 (d, 1H, J = 8.29), 8.19 (d, 1H, J = 8.25), 8.23~8.26 (m, 4H) |
| 3 | C$_{44}$H$_{30}$N$_2$ M + 587.24 | δ□ = 7.36 (dd, 2H, J = 6.55), 7.62 (dd, 2H, J = 7.92), 7.67~7.69 (m, 8H), 7.78~7.82(m, 4H), 7.89~7.91 (m, 6H), 7.96~7.98 (m, 4H), 8.05 (dd, 2H, J = 8.02) 8.35 (dd, 2H, J = 2.60) |
| 4 | C$_{44}$H$_{30}$N$_2$ M + 587.24 | δ□ = 7.49 (dd, 2H, J = 8.33), 7.51 (m, 4H), 7.62~7.70 (m, 6H), 7.85 (dd, 2H, J = 8.14), 7.89~7.92 (m, 4H), 7.95~7.96 (m, 4H), 8.01 (dd, 2H, J = 8.36), 8.08 (dd, 2H, J = 7.45), 8.14 (dd, 2H, J = 8.36), 8.23 (dd, 2H, J = 1.91) |
| 5 | C$_{30}$H$_{20}$N$_4$ M + 437.17 | δ = 7.50 (dd, 2H, J = 6.74), 7.67 (dd, 2H, J = 8.69), 7.78 (dd, 2H, J = 6.60), 7.94 (dd, 2H, J = 8.38), 7.97~8.00 (m, 6H), 8.08 (dd, 2H, J = 8.38), 8.47~8.51 (m, 4H) |
| 6 | C$_{30}$H$_{20}$N$_4$ M + 437.17 | δ = 7.60~7.62 (m, 4H), 7.90~7.93 (m, 4H), 7.98~7.99 (m, 4H), 8.06(dd, 2H, J = 8.39), 8.36 (d, 2H, J = 2.58), 8.51 (d, 2H, J = 6.22), 9.29 (d, 2H, J = 5.42) |
| 7 | C$_{28}$H$_{18}$N$_2$S$_2$ M + 447.09 | δ□ = 7.31 (d, 2H, J = 1.75), 7.57 (dd, 2H, J = 8.57), 7.66 (dd, 2H, J = 6.46), 7.83~7.86 (m, 4H), 7.95 (dd, 2H, J = 8.36), 8.01 (dd, 2H, J = 8.04), 8.06~8.07 (m, 4H) |
| 8 | C$_{28}$H$_{18}$N$_2$O$_2$ M + 415.14 | δ□ = 7.14 (d, 2H, J = 1.75), 7.58~7.60 (m, 4H), 7.83~7.86 (m, 6H), 8.01(dd, 2H, J = 8.04), 8.06~8.07 (m, 4H) |
| 9 | C$_{30}$H$_{22}$N$_2$S$_2$ M + 547.12 | δ□ = 7.28 (d, 1H, J = 7.90), 7.56~7.62 (m, 5H), 7.76 (dd, 2H, J = 8.16), 7.87 (dd, 2H, J = 2.28), 7.99~8.10 (m, 8H), 8.32 (dd, 2H, J = 7.48), 8.48 (dd, 2H, J = 2.38) |
| 10 | C$_{36}$H$_{22}$N$_2$O$_2$ M + 515.17 | δ□ = 7.57~7.62 (m, 6H), 7.80 (dd, 2H, J = 6.62), 7.88 (dd, 2H, J = 2.29), 7.93 (dd, 2H, J = 7.44), 8.05~8.10 (m, 8H), 8.57 (d, 2H, J = 4.71) |
| 11 | C$_{38}$H$_{24}$N$_4$ M + 537.20 | δ□ = 7.65~7.72 (m, 6H), 7.94 (d, 2H, J = 1.95), 8.02~8.16 (m, 10H), 8.32 (dd, 2H, J = 6.63), 8.53 (d, 1H, J = 2.02), 8.68 (d, 1H, J = 1.99), 9.51 (dd, 1H, J = 4.94), 9.61 (dd, 1H, J = 5.46) |
| 12 | C$_{50}$H$_{38}$N$_2$ M + 667.30 | δ = 2.09 (s, 6H), 7.24 (dd, 2H, J = 8.42), 7.28~7.31 (m, 4H), 7.43 (d, 1H, J = 8.47), 7.47 (dd, 2H, J = 1.75), 7.57 (d, 1H, J = 7.55), 7.73~7.76 (m, 4H), 7.81~7.83 (m, 2H), 7.90 (m, 4H), 7.97 (dd, 2H, J = 8.01), 8.04 (dd, 2H, J = 8.40), 8.34 (dd, 2H, J = 2.58) |
| 13 | C$_{56}$H$_{36}$N$_4$ M + 765.29 | δ□ = 7.37 (dd, 1H, J = 7.54), 7.52 (t, 1H, J = 7.51), 7.57~7.64 (m, 6H), 7.74 (dd, 2H, J = 8.70), 7.81~7.90 (m, 8H), 8.15 (dd, 2H, J = 5.52), 8.23~8.26 (m, 4H), 8.30~8.36 (m, 6H), 8.42 (dd, 2H, J = 5.49), 8.52~8.58 (m, 4H) |
| 14 | C$_{50}$H$_{32}$N$_8$ M + 745.27 | δ□ = 7.27 (m, 4H), 7.52(dd, 2H, J = 7.51), 7.66~7.71 (m, 4H), 7.95~8.07 (m, 12H), 8.14~8.18 (m, 4H), 8.27 (dd, 2H, J = 6.97), 8.29~8.32 (m, 4H) |
| 15 | C$_{32}$H$_{12}$D$_{10}$N$_2$ M + 445.24 | δ□ = 7.30~7.35 (m, 2H), 7.46~7.52 (m, 2H), 7.63~7.70 (m, 4H), 7.75~7.80 (m, 2H), 8.00~8.03 (m, 2H) |
| 16 | C$_{36}$H$_{30}$N$_2$O$_4$ M + 555.22 | δ□ = 3.68 (s, 12H), 6.21 (dd, 2H, J = 1.80), 7.14 (dd, 2H, J = 1.80), 7.19 (dd, 2H, J = 1.81), 7.62 (dd, 2H, J = 8.67), 7.84~8.01 (m, 8H), 8.31 (dd, 2H, J = 2.50) |
| 17 | C$_{44}$H$_{30}$N$_2$ M + 587.24 | δ □ = 7.43 (dd, 2H, J = 7.32), 7.53~7.67 (m, 14H), 7.88~8.07 (m, 10H), 8.20 (d, 2H, J = 8.23), 8.36 (dd, 2H, J = 1.83) |
| 18 | C$_{36}$H$_{30}$N$_2$ M + 491.24 | δ = 1.38 (t, 6H, J = 7.12), 4.60 (q, 4H, J = 7.11), 7.40 (dd, 4H, J = 1.75), 7.47~7.60 (m, 10H), 7.80~7.90 (m, 8H) |
| 19 | C$_{32}$H$_{12}$F$_{10}$N$_2$ M + 615.08 | δ□ = 7.46 (t, 1H, J = 7.84), 7.61 (t, 1H, J = 7.53), 7.87(d, 2H, J = 2.18), 7.93~7.99 (m, 6H), 8.05 (dd, 2H, J = 8.22) |
| 20 | C$_{34}$H$_{28}$N$_4$ M + 493.23 | δ□ = 1.37 (t, 6H, J = 7.13), 4.64 (q, 4H, J = 7.11), 7.56 (dd, 2H, J = 8.76), 7.64 (q, 2H, J = 1.75), 7.76 (dd, 2H, J = 8.76), 7.82 (dd, 2H, J = 1.75), 7.94 (m, 2H), 8.10~8.19 (m, 4H), 8.50~8.56 (m, 4H) |
| 21 | C$_{40}$H$_{26}$N$_6$ M + 591.22 | δ □ = 7.37~7.45 (m, 2H), 7.52 (dd, 2H, J = 8.23), 7.58~7.64 (m, 4H), 7.84 (dd, 2H, J = 8.22), 7.89~7.93 (m, 4H), 8.03 (dd, 2H, J = 1.74), 8.05~8.08 (m, 4H), 8.24 (dd, 2H, J = 8.23), 8.80 (dd, 2H, J = 1.99), 9.16 (dd, 2H, J = 1.99), 9.30 (dd, 2H, J = 2.00) |
| 22 | C$_{32}$H$_{26}$N$_2$S$_2$ M + 503.15 | δ = 1.52 (t, 6H, J = 6.80), 4.59 (q, 4H, J = 6.81), 7.41 (dd, 2H, J = 9.35), 7.56~7.59 (m, 2H), 7.60~7.63 (m, 4H), 7.78 (dd, 2H, J = 6.24), 7.83 (dd, 2H, J = 1.98), 7.90 (dd, 2H, J = 1.82), 8.09 (q, 2H, J = 2.33) |
| 23 | C$_{48}$H$_{34}$N$_2$S$_2$ M + 703.22 | δ □ = 1.51 (t, 6H, J = 2.67), 4.88 (q, 4H, J = 2.66), 7.51 (t, 2H, J = 5.98), 7.75~7.86 (m, 8H), 7.95 (dd, 2H, J = 6.78), 8.24~8.35 (m, 6H), 8.38~8.41 (m, 4H), 8.49~8.53 (m, 2H) |
| 24 | C$_{56}$H$_{34}$N$_2$O$_2$ M + 767.26 | δ □ = 7.53~7.64 (m, 6H), 7.85 (dd, 2H, J = 5.03), 7.86 (dd, 2H, J = 8.55), 7.88~7.93 (m, 2H), 7.96~8.21 (m, 12H), 8.34~8.37 (m, 2H), 8.45~8.50 (m, 4H), 8.59~8.68 (m, 4H) |

-continued

| Compound Number | LC-MS | ¹H NMR (CD$_2$Cl$_2$, 300 MHz) |
|---|---|---|
| 25 | C$_{36}$H$_{30}$N$_2$ M + 491.24 | δ = 1.37 (t, 6H, J = 7.13), 4.77 (q, 4H, J = 7.11), 7.45 (dd, 2H, J = 9.10), 7.47 (t, 2H, J = 8.11), 7.53~7.63 (m, 8H), 7.70~7.74 (m, 2H), 7.76~7.79 (m, 2H), 7.83~7.88 (m, 2H), 8.44~8.53 (m, 2H) |
| 26 | C$_{48}$H$_{34}$N$_2$S$_2$ M + 703.22 | δ = 1.54 (t, 6H, J = 2.67), 5.03 (q, 4H, J = 2.67), 7.61 (t, 2H, J = 5.82), 7.74~7.88 (m, 8H), 7.91~7.98 (m, 4H), 8.13~8.18 (m, 2H), 8.33~8.41 (m, 4H), 8.39~8.52 (m, 2H), 8.82~8.87 (m, 2H) |
| 27 | C$_{54}$H$_{46}$N$_2$ M + 723.37 | δ = 1.36 (t, 6H, J = 6.99), 2.11 (s, 12H), 5.17 (q, 4H, J = 6.99), 7.31~7.37 (m, 2H), 7.51~7.65 (m, 8H), 7.74~7.79 (m, 6H), 7.90~7.95 (m, 6H), 8.51 (dd, 2H, J = 2.69) |
| 28 | C$_{42}$H$_{28}$N$_4$ M + 589.23 | δ = 7.40~7.44 (m, 2H), 7.51~7.60 (m, 6H), 7.71~7.79 (m, 2H), 7.84 (dd, 2H, J = 8.22), 7.89~7.93 (m, 4H), 7.99~8.08 (m, 6H), 8.63~8.66 (m, 2H), 8.77 (dd, 2H, J = 2.23), 9.13 (dd, 2H, J = 2.76) |
| 29 | C$_{60}$H$_{44}$N$_4$ M + 820.36 | δ = 1.53 (t, 6H, J = 2.67), 5.28 (q, 4H, J = 2.67), 7.49~7.60 (m, 8H), 7.71 (dd, 2H, J = 7.22), 7.79~7.95 (m, 10H), 8.16~8.29 (m, 4H), 8.39~8.47 (m, 6H), 8.78 (dd, 2H, J = 4.77), 8.83 (dd, 2H, J = 4.77) |
| 30 | C$_{52}$H$_{34}$N$_6$ M + 743.28 | δ = 7.11~7.18 (m, 1H), 7.31~7.42 (m, 3H), 7.58~7.60 (m, 4H), 7.61~7.63 (m, 2H), 7.82~7.86 (m, 4H), 7.91~8.06 (m, 10H), 8.09~8.12 (m, 2H), 8.18~8.21 (m, 2H), 8.28~8.30 (m, 2H), 9.64 (d, 2H, J = 1.99), 9.75 (d, 2H, J = 1.99) |
| 31 | C$_{52}$H$_{34}$N$_6$ M + 743.28 | δ = 7.26~7.34 (m, 5H), 7.57~7.64 (m, 4H), 7.83~7.95 (m, 5H), 8.06~8.16 (m, 10H), 8.28 (d, 2H, J = 1.51), 8.58 (d, 2H, J = 8.46), 8.84 (dd, 2H, J = 1.99), 9.03~9.07 (m, 2H), 9.25 (dd, 2H, J = 1.96) |
| 32 | C$_{44}$H$_{30}$N$_2$ M + 587.24 | δ = 7.49~7.78 (m, 14H), 7.91 (dd, 2H, J = 8.02), 7.95 (dd, 2H, J = 2.23), 8.00~8.07 (m, 6H), 8.19~8.23 (m, 4H), 8.28 (dd, 2H, J = 8.38) |
| 33 | C$_{56}$H$_{34}$N$_2$O$_2$ M + 767.26 | δ = 7.74~7.83 (m, 5H), 7.88~7.93 (m, 3H), 8.13~8.18 (m, 2H), 8.60 (dd, 2H, J = 5.04), 8.65~8.77 (m, 8H), 8.81~8.99 (m, 12H), 9.03~9.07 (m, 2H) |
| 34 | C$_{54}$H$_{36}$N$_4$ M + 741.29 | δ = 7.54~7.61 (m, 2H), 7.74~7.80 (m, 4H), 7.87~7.93 (m, 8H), 8.07~8.09 (m, 2H), 8.12~8.17 (m, 6H), 8.23~8.29 (m, 2H), 8.32~8.36 (m, 6H), 8.40~8.46 (m, 2H), 8.50~8.57 (m, 4H) |
| 35 | C$_{42}$H$_{28}$N$_4$ M + 589.23 | δ = 7.50~7.70 (m, 12H), 8.00~8.06 (m, 4H), 8.15 (dd, 2H, J = 8.44), 8.22~8.26 (m, 4H), 8.30 (dd, 2H, J = 8.38), 8.83~8.89 (m, 4H) |
| 36 | C$_{44}$H$_{30}$N$_2$ M + 587.24 | δ = 7.51 (dd, 2H, J = 7.45), 7.54 (dd, 2H, J = 7.77), 7.60 (q, 4H, J = 8.15), 7.61~7.67 (m, 6H), 7.90 (dd, 2H, J = 8.15), 7.92~8.04 (m, 8H), 8.10 (dd, 2H, J = 8.49), 8.26 (dd, 2H, J = 8.48), 8.31 (dd, 2H, J = 8.50) |
| 37 | C$_{42}$H$_{28}$N$_4$ M + 589.23 | δ = 7.50 (t, 1H, J = 7.79), 7.52 (t, 1H, J = 8.39), 7.55~7.64 (m, 4H), 7.87~7.94 (m, 4H), 7.98 (dd, 2H, J = 8.51), 8.09~8.13 (m, 2H), 8.18~8.24 (m, 5H), 8.5~8.29 (m, 2H), 8.37 (q, 2H, J = 8.49), 8.39 (dd, 2H, J = 8.51), 9.07~9.14 (m, 4H) |
| 38 | C$_{44}$H$_{34}$N$_2$ M + 591.27 | δδ = 1.47 (t, 6H, J = 7.06), 4.63 (q, 4H, J = 7.05), 7.56 (dd, 2H, J = 6.75), 7.69~7.81 (m, 5H), 7.85 (dd, 1H, J = 6.58), 7.88 (dd, 1H, J = 6.57), 7.90 (dd, 2H, J = 7.18), 8.06~8.10 (m, 4H), 8.14 (dd, 2H, J = 7.18), 8.15~8.21 (m, 3H), 8.27~8.31 (m, 1H), 8.55~8.59 (m, 2H) |
| 39 | C$_{56}$H$_{30}$F$_4$N$_2$S$_2$ M + 871.18 | δ = 7.32 (dd, 2H, J = 1.92), 7.71 (dd, 2H, J = 1.74), 7.78 (dd, 1H, J = 8.36), 7.83 (dd, 1H, J = 8.39), 8.01~8.14 (m, 6H), 8.32 (dd, 2H, J = 8.38), 8.61~8.65 (m, 2H), 8.70~8.75 (m, 4H), 8.84 (dd, 2H, J = 5.39), 8.92~8.98 (m, 4H), 9.05~9.10 (m, 4H) |
| 40 | C$_{52}$H$_{34}$N$_6$ M + 743.28 | δ = 7.38 (dd, 3H, J = 7.83), 7.51~7.58 (m, 2H), 7.65 (dd, 1H, J = 8.40), 7.87 (dd, 2H, J = 6.78), 7.91~7.93 (m, 4H), 8.11 (dd, 2H, J = 5.25), 8.18~8.35 (m, 11H), 8.40 (dd, 1H, J = 6.21), 8.50 (dd, 2H, J = 6.92), 8.63 (dd, 2H, J = 6.21), 8.78~8.83 (m, 2H), 9.40~9.44 (m, 2H) |
| 41 | C$_{44}$H$_{30}$N$_2$ M + 587.24 | δ = 7.30~7.34 (m, 2H), 7.60~7.73 (m, 12H), 7.89~7.97 (m, 8H), 8.01 (dd, 2H, J = 8.22), 8.06 (dd, 2H, J = 8.44), 8.22 (dd, 2H, J = 8.44), 8.68 (dd, 2H, J = 1.99) |
| 42 | C$_{44}$H$_{32}$N$_4$O$_2$ M + 649.25 | δ = 3.80 (s, 6H), 7.03 (dd, 4H, J = 8.72), 7.69~7.78 (m, 4H), 7.81~7.90 (m, 3H), 7.94 (dd, 1H, J = 8.70), 7.96 (dd, 2H, J = 1.99), 7.98 (dd, 2H, J = 2.19), 8.05 (dd, 2H, J = 8.44), 8.26 (dd, 2H, J = 8.45), 8.45 (dd, 2H, J = 5.09), 8.76 (dd, 2H, J = 2.19), 9.35 (dd, 2H, J = 3.05) |
| 43 | C$_{48}$H$_{38}$N$_2$ M + 643.30 | δ = 1.50 (t, 6H, J = 6.73), 4.60 (q, 4H, J = 6.73), 7.53~7.57 (m, 2H), 7.60~7.71 (m, 12H), 7.73~7.84 (m, 4H), 8.00~8.13 (m, 4H), 8.50~8.53 (m, 2H), 8.63~8.66 (m, 2H) |
| 44 | C$_{56}$H$_{40}$N$_4$ M + 769.33 | δ = 6.88~6.92 (m, 8H), 7.19~7.39 (m, 16H), 7.53 (dd, 2H, J = 1.81), 7.55 (dd, 4H, J = 8.23), 7.82~7.96 (m, 10H) |
| 45 | C$_{56}$H$_{44}$N$_4$ M + 773.36 | δ = 1.35 (t, 6H, J = 7.00), 4.54 (q, 4H, J = 7.00), 6.90~6.94 (m, 4H), 7.14 (dd, 1H, J = 8.23), 7.16 (dd, 1H, J = 8.22), 7.19~7.49 (m, 20H), 7.68 (dd, 2H, J = 5.33), 7.76~7.84 (m, 6H) |

-continued

| Compound Number | LC-MS | $^1$H NMR (CD$_2$Cl$_2$, 300 MHz) |
|---|---|---|
| 46 | C$_{72}$H$_{50}$N$_6$ M + 999.41 | δ = 6.59~6.93 (m 8H), 7.19~7.35 (m, 17H), 7.40~7.56 (m, 9H), 7.60 (dd, 2H, J = 8.40), 7.84~7.89 (m, 4H), 7.92~7.98 (m, 4H), 8.00~8.08 (m, 4H), 8.13 (dd, 2H, J = 6.35) |
| 47 | C$_{56}$H$_{36}$N$_4$ M + 765.29 | δ = 7.29~7.33 (m, 1H), 7.53~7.66 (m, 13H), 7.88 (dd, 2H, J = 8.58), 8.02 (dd, 2H, J = 6.98), 8.11 (dd, 2H, J = 5.52), 8.19~8.28 (m, 12H), 8.50 (dd, 2H, J = 4.40), 8.55 (dd, 2H, J = 5.52) |
| 48 | C$_{37}$H$_{23}$N$_3$S M + 542.16 | δ = 7.48~7.52 (m, 1H), 7.60~7.63 (m, 1H), 7.69~7.84 (m, 4H), 7.99~8.26 (m, 12H), 8.33~8.35 (m, 1H), 8.42~8.45 (m, 1H), 8.49~8.52 (m, 2H), 8.69~8.73 (m, 1H) |
| 49 | C$_{44}$H$_{28}$N$_2$O M + 601.22 | δ = 7.53~7.68 (m, 1H), 7.60~7.61 (m, 1H), 7.63~7.65 (m, 2H), 7.69~7.79 (m 4H), 7.82~7.90 (m, 3H), 7.95~7.99 (m, 3H), 8.01~8.32 (m, 13H), 8.57~8.62 (m, 1H) |
| 50 | C$_{50}$H$_{31}$N$_3$S M + 706.22 | δ = 7.31~7.36 (m, 1H), 7.68~7.77 (m, 5H), 7.80~7.92 (m, 6H), 8.80 (dd, 1H, J = 5.54), 8.09~8.37 (m, 15H), 8.39 (dd, 1H, J = 5.34), 8.64~8.70 (m, 1H) |
| 51 | C$_{41}$H$_{27}$N$_5$ M + 590.23 | δ = 7.44 (t, 1H, J = 7.78), 7.51 (dd, 1H, J = 8.23), 7.54 (dd, 1H, J = 8.23), 7.60~7.72 (m, 6H), 7.86~8.09 (m, 12H), 8.10~8.24 (m, 4H), 8.31 (dd, 2H, J = 8.29) |
| 52 | C$_{54}$H$_{36}$N$_4$ M + 741.29 | δ = 7.48 (t, 2H, J = 7.43), 7.53 (dd, 2H, J = 8.55), 7.59~7.64 (m, 8H), 7.68~7.73 (m, 4H), 7.88 (dd, 2H, J = 7.89), 7.92 (dd, 2H, J = 8.00), 7.99 (dd, 2H, J = 1.76), 8.06~8.14 (m, 4H), 8.19~8.25 (m, 4H), 8.42~8.46 (m, 2H), 8.89~8.93 (m. 2H), 9.19~9.24 (m, 2H) |
| 53 | C$_{61}$H$_{39}$N$_5$ M + 842.32 | δ = 7.35~7.41 (m, 2H), 7.65~7.70 (m, 1H), 7.74 (dd, 1H, J = 7.75), 7.80~8.01 (m, 11H), 8.05~8.09 (m, 6H), 8.12 (dd, 2H, J = 3.76), 8.20~8.25 (m, 4H), 8.28~8.30 (m, 2H), 8.46~8.50 (m, 2H), 8.55~8.58 (m, 1H), 8.66~8.71 (m, 3H), 8.83~8.85 (m, 1H), 9.40~9.45 (m, 2H), 9.49~9.52 (m, 1H) |
| 54 | C$_{53}$H$_{45}$N$_5$ M + 752.37 | δ = 1.62 (s, 9H), 1.63 (s, 9H), 7.35~7.42 (m, 2H), 7.46~7.57 (m, 3H), 7.68~7.72 (m, 1H), 7.80~7.99 (m, 8H), 8.09~8.20 (m, 4H), 8.29~8.34 (m, 1H), 8.65~8.71 (m, 2H), 8.74~8.80 (m, 2H), 8.90~8.95 (m, 1H), 9.32~9.36 9m, 1H), 9.38 (dd, 1H, J = 5.04) |
| 55 | C$_{60}$H$_{42}$N$_2$S$_2$ M + 855.28 | δ = 2.11 (t, 6H, J = 6.94), 4.82 (q, 4H, J = 6.93), 7.60~7.63 (m, 2H), 7.69~7.76 (m, 6H), 7.95~7.98 (m, 2H), 8.02~8.07 (m, 3H), 8.14~8.17 (m, 1H), 8.29~8.32 (m, 2H), 8.64 (dd, 2H, J = 5.47), 8.69 (dd, 2H, J = 5.00), 8.71~8.75 (m, 4H), 8.85 (d, 2H, J = 5.13), 9.02 (dd, 2H, J = 5.47), 9.09 (dd, 2H, J = 5.47), 9.19 (dd, 2H, J = 5.37) |
| 56 | C$_{43}$H$_{29}$N$_3$ M + 588.24 | δ = 7.39~7.45 (m, 2H), 7.47~7.52 (m, 1H), 7.58 (t, 1H, J = 8.02), 7.60~7.65 (m, 5H), 7.70~7.73 (m, 1H), 7.80~7.85 (m, 2H), 7.89~7.93 (m, 5H), 7.99~8.08 (m, 3H), 8.19~8.24 (m, 3H), 8.30 (q, 1H, J = 1.93), 8.36 (dd, 1H, J = 1.82), 8.62~8.65 (m, 1H) |
| 57 | C$_{46}$H$_{30}$N$_4$ M + 639.25 | δ = 7.29~7.37 (m, 2H), 7.52 (dd, 1H, J = 8.23), 7.56 (dd, 1H, J = 7.89), 7.58~7.72 (m, 5H), 7.82~7.86 (m, 2H), 7.90~7.92 (m, 1H), 7.93~7.95 (m, 3H), 7.98~8.03 (m, 1H), 8.06 (dd, 1H, J = 7.87), 8.09~8.14 (m, 1H), 8.17 (dd, 1H, J = 6.45), 8.20~8.25 (m, 3H), 8.28~8.33 (m, 3H), 8.43~8.45 (m, 1H), 8.51~8.55 (m, 1H), 8.63~8.65 (m, 1H), 9.28~9.32 (m, 1H) |
| 58 | C$_{40}$H$_{26}$N$_2$ M + 535.21 | δ = 7.31~7.38 (m, 6H), 7.49 (dd, 2H, J = 8.82), 7.52 (dd, 2H, J = 8.47), 7.58~7.66 (m, 12H), 7.71~7.73 (m, 2H), 7.84~7.87 (m, 2H) |
| 59 | C$_{48}$H$_{36}$N$_4$ M + 669.29 | δ = 1.64 (t, 6H, J = 2.67), 5.19 (q, 4H, J = 2.66), 7.30~7.35 (m, 2H), 7.53~7.55 (m, 2H), 7.58~7.65 (m, 4H), 7.70~7.77 (m, 2H), 7.82~7.84 (m, 1H), 7.91~8.06 (m, 9H), 8.32~8.38 (m, 6H) |
| 60 | C$_{38}$H$_{24}$N$_4$ M + 537.20 | δ = 7.32~7.38 (m, 2H), 7.50~7.54 (m, 4H), 7.59~7.65 (m, 4H), 7.66 (dd, 1H, J = 7.80), 7.74 (dd, 1H, J = 7.80), 7.78~7.84 (m, 4H), 7.90~7.94 (m, 4H), 8.40 (dd, 2H, J = 5.35), 9.27~9.32 (m, 2H) |
| 61 | C$_{42}$H$_{26}$N$_2$O M + 575.20 | δ = 6.80~6.82 (m, 1H), 7.13~7.16 (m, 1H), 7.26~7.39 (m, 4H), 7.44~7.75 (m, 18H), 7.86 (dd, 1H, J = 8.83), 8.10~8.13 (m, 1H) |
| 62 | C$_{52}$H$_{34}$N$_2$ M + 687.27 | δ = 7.19~7.24 (m, 2H), 7.31~7.34 (m, 2H), 7.38~7.42 (m, 4H), 7.46~7.69 (m, 16H), 7.75 (dd, 2H, J = 1.91), 7.79~7.84 (m, 4H), 7.94~7.98 (m 2H), 8.55~8.57 (m, 2H) |
| 63 | C$_{58}$H$_{36}$N$_4$ M + 789.29 | δ = 7.19~7.21 (m, 1H, J = 7.83), 7.32~7.37 (m, 1H), 7.49~7.70 (m, 14H), 7.86~7.95 (m, 4H), 8.03~8.10 (m, 6H), 8.28~8.32 (m, 2H), 8.42 (dd, 2H, J = 5.64), 8.48 (dd, 2H, J = 5.64), 8.78~8.80 (m, 2H), 9.34~9.39 (m, 2H) |
| 64 | C$_{58}$H$_{42}$N$_6$ M + 823.35 | δ = 2.01 (t, 6H, J = 6.95), 5.30 (q, 4H, J = 6.95), 7.60~7.68 (m, 5H), 7.74~7.78 (m, 1H), 7.92~7.95 (m, 4H), 8.31~8.33 (m, 1H), 8.48~8.50 (m, 4H), 8.53~8.58 (m, 1H), 8.60~8.65 (m, 5H), 8.69 (dd, 1H, J = 5.28), 8.70 (dd, 1H, J = 5.26), 8.80~8.82 (m, 2H), 9.07~9.10 (m, 2H), 9.10~9.14 (m, 2H), 9.19~9.23 (m, 2H) |
| 65 | C$_{56}$H$_{42}$F$_2$N$_4$ M + 809.34 | δ = 1.07 (t, 6H, J = 7.03), 4.53 (q, 4H, J = 7.03), 6.97 (dd, 2H, J = 8.90), 7.00 (dd, 2H, J = 8.75), 7.16~7.36 (m, 22H), 7.51~7.54 (m, 2H), 7.58~7.64 (m, 4H) |

-continued

| Compound Number | LC-MS | $^1$H NMR (CD$_2$Cl$_2$, 300 MHz) |
|---|---|---|
| 66 | C$_{58}$H$_{48}$N$_4$O$_2$ M + 833.38 | δ = 1.39 (t, 6H, 7.11) 3.80 (s, 6H), 4.79 (q, 4H, J = 7.10), 6.46 (dd, 2H, J = 8.53), 6.99 (d, 1H, J = 8.42), 7.02 (d, 1H, J = 8.46), 7.17~7.30 (m, 15H), 7.37 (dd, 2H, J = 1.80), 7.56 (dd, 1H, J = 3.17), 7.57~7.62 (m, 6H), 7.80 (dd, 2H, J = 8.42), 7.95 (dd, 1H, J = 8.53), 8.13~8.16 (m, 1H) |
| 67 | C$_{46}$H$_{28}$N$_2$S M + 641.20 | δ = 7.33~7.38 (m, 3H), 7.48 (dd, 2H, J = 8.83), 7.50 (dd, 1H, J = 8.82), 7.53~7.69 (m, 14H), 7.73~7.79 (m, 3H), 7.84~7.89 (m, 3H), 8.06 (dd, 1H, J = 7.74), 8.12 (dd, 1H, J = 3.75) |
| 68 | C$_{64}$H$_{48}$N$_4$S$_2$ M + 937.33 | δ = 1.76 (t, 6H, J = 6.80), 2.20 (t, 6H, J = 6.94), 5.10 (q, 4H, J = 6.94), 5.23 (q, 4H, J = 6.80), 8.08~8.14 (m, 3H), 8.41~8.43 (m, 2H), 8.47~8.51 (m, 3H), 8.56 (dd, 2H, J = 5.14), 8.66 (dd, 2H, J = 5.13), 8.69~8.8.86 (m, 11H), 8.92~8.95 (m, 3H), 9.04~9.10 (m, 2H), 9.13~9.16 (m, 2H) |
| 69 | C$_{48}$H$_{40}$N$_4$O$_2$ M + 705.32 | δ = 1.54 (t, 6H, J = 2.67), 1.72 (t, 6H, J = 2.66), 4.90 (q, 4H, J = 2.67), 5.02 (q, 4H, J = 2.66), 6.84 (dd, 2H, J = 3.00), 6.92 (dd, 2H, J = 2.99), 7.44~7.51 (m, 4H), 7.70~7.77 (m, 4H), 7.87 (dd, 1H, J = 5.88), 8.05 (dd, 1H, J = 5.81), 8.19 (d, 1H, J = 5.21), 8.39 (d, 1H, J = 5.53), 8.47 (d, 1H, J = 4.08), 8.83 (d, 1H, J = 4.37), 9.08~9.11 (m, 2H) |

Example 1

An anode was prepared by cutting a Corning 15 Ω/m$^2$ (1200 Å) ITO glass substrate to a size of 50 mm×50 mm×0.7 mm, ultrasonically cleaning the glass substrate using isopropyl alcohol and pure water for five minutes each, and, then irradiating UV light for 30 minutes and exposing to ozone to clean. Then, the glass substrate was disposed in a vacuum deposition apparatus.

Then, 2-TNATA, which is a known material for forming a HIL, was vacuum deposited on the glass substrate to form a HIL having a thickness of 600 Å, and then 4,4'-bis[N-(1-naphthyl)-N-phenylamino]biphenyl (NPB), as a hole transporting compound, was vacuum deposited on the HIL to form a HTL having a thickness of 300 Å.

2-TNATA

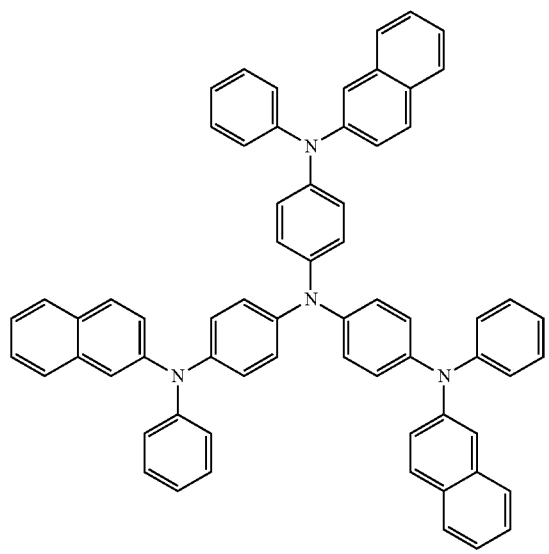

-continued

NPB

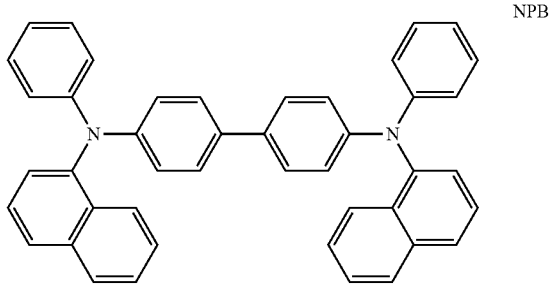

DNA

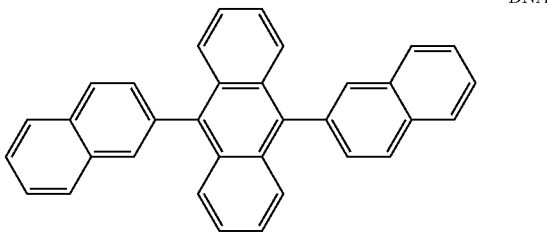

DPVBi

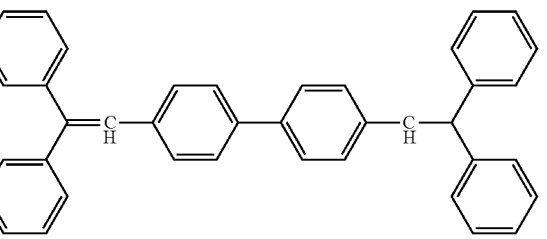

Then, Compound 21, as a blue fluorescent host, and 1,4-bis-(2,2-diphenylvinyl)biphenyl (DPVBi), as a known blue fluorescent dopant, were deposited simultaneously with a weight ratio of 98:2, on the HTL, to form an EML having a thickness of 300 Å.

Then, Alq$_3$ was deposited on the EML to form an ETL having a thickness of 300 Å, and then LiF, which is a halogenated alkali metal, was deposited on the ETL to form an EIL having a thickness of 10 Å. Then, Al was vacuum deposited on the EIL to form a cathode having a thickness of 3,000

Å, thereby forming an LiF/Al electrode. As a result, an organic light-emitting device was manufactured.

Example 2

An organic light-emitting device was manufactured in the same manner as in Example 1, except that Compound 29 was used instead of Compound 21 to form the EML.

Example 3

An organic light-emitting device was manufactured in the same manner as in Example 1, except that Compound 1 was used instead of a known compound NPB to form the HTL, and a known compound 9,10-di-naphthalene-2-yl-anthracene (hereinafter, referred to as DNA) was used as a blue fluorescent host and a known compound 1,4-bis-(2,2-diphenylvinyl)biphenyl (hereinafter, referred to as DPVBi) was used as a blue fluorescent dopant on the HTL.

Example 4

An organic light-emitting device was manufactured in the same manner as in Example 3, except that Compound 4 was used in stead of Compound 1 to form the HTL.

Example 5

An organic light-emitting device was manufactured in the same manner as in Example 3, except that Compound 17 was used instead of Compound 1 to form the HTL.

Example 6

An organic light-emitting device was manufactured in the same manner as in Example 3, except that Compound 25 was used instead of Compound 1 to form the HTL.

Example 7

An organic light-emitting device was manufactured in the same manner as in Example 3, except that Compound 44 was used instead of Compound 1 to form the HTL.

Example 8

An organic light-emitting device was manufactured in the same manner as in Example 1, except that a known compound DNA was used as a blue fluorescent host and a known compound DPVBi was used as a blue fluorescent dopant to form the EML, and Compound 14 was used on the ETL instead of a known compound $Alq_3$ to form the ETL.

Example 9

An organic light-emitting device was manufactured in the same manner as in Example 8, except that Compound 37 was used instead of Compound 14.

Example 10

An organic light-emitting device was manufactured in the same manner as in Example 1, except that Compound 4 was used instead of a known compound NPB to form the HTL, and Compound 21 was used as a blue fluorescent host and a known compound DPVBi was used as a blue fluorescent dopant on the HTL.

Example 11

An organic light-emitting device was manufactured in the same manner as in Example 1, except that Compound 44 was used instead of a known compound NPB to form the HTL, and Compound 29 was used as a blue fluorescent host and a known compound DPVBi was used as a blue fluorescent dopant on the HTL.

Example 12

An organic light-emitting device was manufactured in the same manner as in Example 1, except that Compound 4 was used instead of a known compound NPB to form the HTL, Compound 29 was used as a blue fluorescent host and a known compound DPVBi was used as a blue fluorescent dopant on the HTL, and Compound 37 was used to form the ETL on the EML.

Comparative Example 1

An organic light-emitting device was manufactured in the same manner as in Example 1, except that a known blue fluorescent host DNA was used instead of Compound 21 to form the EML.

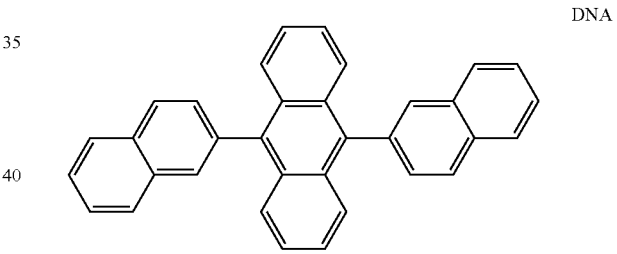

DNA

When the compound represented by Formula 1 according to an embodiment of the present embodiment was used as a host, a dopant, an electron transporting material or a hole transporting material of the organic light-emitting device, driving voltage of the organic light-emitting device was reduced by 1 V or more than DNA, DPVBi, NPB, and Alq3 which are known materials, efficiency was considerably increased, thereby providing excellent I-V-L characteristics, and increasing a lifespan. When the compound represented according to the present embodiment was used as a host of the organic light-emitting devices prepared in Examples 1 and 2, driving voltage was reduced by 1.4 V or more, efficiency was increased, and lifespan was increased compared to the organic light-emitting device of Comparative Example 1. When the compound represented according to an embodiment of the present embodiment was used as a hole transporting material of the organic light-emitting devices prepared in Examples 3 to 7, driving voltage was reduced by 1 V or more, efficiency was increased, and lifespan was increased compared to the organic light-emitting device of Comparative Example 1. When the compound represented according to an embodiment of the present embodiment was used as an electron transporting material of the organic light-emitting devices prepared in Examples 8 and 9, driving voltage was reduced by 1.7 V or more, efficiency was increased, and lifespan was increased by 180% compared to the organic light-emitting device of Comparative Example 1. When the compound represented according to an embodiment of the present embodiment was used as a host and a hole transporting material of the organic light-emitting devices prepared in Examples 10 to 12, driving voltage was reduced by 1.7 V or more, efficiency was increased by 150% or more, and lifespan was increased by 200% compared to the organic light-emitting device of Comparative Example 1. When the compound represented according to an embodiment of the present embodiment in Example 9 was used as a hole transporting material, a host, and an electron transporting material, driving voltage was reduced by about 2 V, efficiency was increased, and lifespan was increased. Characteristics and lifespan of the organic light-emitting devices are shown in Table 1 below.

The heterocyclic compounds according to embodiments of the present invention have excellent light-emitting characteristics and excellent electron transporting characteristics, and thus may be used as hole injecting materials or hole transporting materials suitable for all-color fluorescent and phosphorescent devices, such as red, green, blue, and white fluorescent and phosphorescent devices. In particular, the heterocyclic compounds are efficiently used as light-emitting materials of green, blue, and while fluorescent devices. By using the heterocyclic compounds, organic light-emitting devices having high efficiency, low driving voltage, high brightness, and long lifespan may be prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

TABLE 1

|  | light-emitting material, electron or hole transporting materials | Driving voltage (V) | Current density (mA/cm$^2$) | Brightness (cd/m$^2$) | Efficiency (cd/A) | Color | Half-life span (hr @100 mA/cm$^2$) |
| --- | --- | --- | --- | --- | --- | --- | --- |
| Example 1 | light-emitting host Compound 21 | 6.45 | 50 | 2,217 | 4.43 | Blue | 198 hr |
| Example 2 | light-emitting host Compound 29 | 6.37 | 50 | 2,331 | 4.66 | Blue | 204 hr |
| Example 3 | Hole transporting Compound 1 | 6.52 | 50 | 2,232 | 4.47 | Blue | 188 hr |
| Example 4 | Hole transporting Compound 4 | 6.61 | 50 | 2,314 | 4.62 | Blue | 187 hr |
| Example 5 | Hole transporting Compound 17 | 6.83 | 50 | 2,156 | 4.31 | Blue | 196 hr |
| Example 6 | Hole transporting Compound 25 | 6.48 | 50 | 2,197 | 4.39 | Blue | 176 hr |
| Example 7 | Hole transporting Compound 44 | 5.94 | 50 | 2,210 | 4.42 | Blue | 181 hr |
| Example 8 | Electron transporting Compound 14 | 6.15 | 50 | 2,433 | 4.87 | Blue | 203 hr |
| Example 9 | Electron transporting Compound 37 | 6.07 | 50 | 2,498 | 4.99 | Bluish green | 210 hr |
| Example 10 | Hole transporting Compound 4, light-emitting host Compound 21 | 5.76 | 50 | 2,398 | 4.79 | Blue | 226 hr |
| Example 11 | Hole transporting Compound 44, light-emitting host Compound 29 | 6.14 | 50 | 2,413 | 4.82 | Blue | 201 hr |
| Example 12 | Hole transporting Compound 4, light-emitting host Compound 29, Electron transporting Compound 37 | 5.87 | 50 | 2,420 | 4.84 | Blue | 214 hr |
| Comparative Example 1 | DNA-DPVBi | 7.85 | 50 | 1,560 | 3.12 | Blue | 113 hr |

What is claimed is:

1. A compound represented by Formula 1 below:

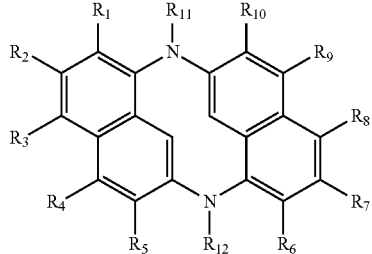

[Formula 1]

wherein, in Formula 1, $R_1$ through $R_{12}$ are each independently a hydrogen atom, a heavy hydrogen atom, a halogen atom, a cyano group, a substituted or unsubstituted $C_1$-$C_{60}$ alkyl group, a substituted or unsubstituted $C_1$-$C_{60}$ alkenyl group, a substituted or unsubstituted $C_6$-$C_{60}$ aryl group, an amino group substituted with a $C_6$-$C_{50}$ aryl group, a substituted or unsubstituted $C_3$-$C_{60}$ heteroaryl group, or a substituted or unsubstituted $C_6$-$C_{60}$ condensed polycyclic group, and wherein, optionally, adjacent substituents from among $R_1$ through $R_5$ or adjacent substituents from among $R_6$ through $R_{10}$ are connected to each other to form a ring.

2. The compound of claim 1, wherein, in Formula 1, $R_1$ to $R_{12}$ are each independently selected from the group consisting of a hydrogen atom, a heavy hydrogen atom, a halogen atom, a cyano group, a substituted or unsubstituted $C_1$-$C_{20}$ alkyl group, and a substituted or unsubstituted $C_1$-$C_{20}$ alkenyl group.

3. The compound of claim 1, wherein, in Formula 1, $R_1$ to $R_{12}$ are each independently one of Formulae 2a to 2i below:

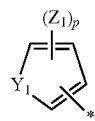

2a

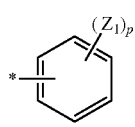

2b

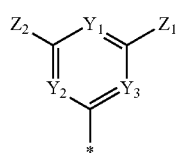

2c

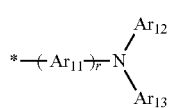

2d

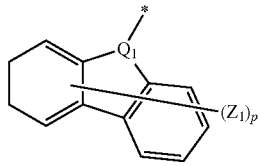

2e

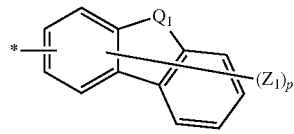

2f

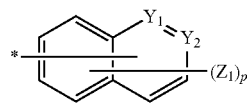

2g

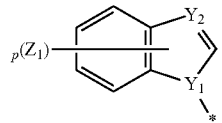

2h

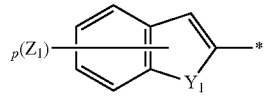

2i wherein, in Formulae 2a to 2i, $Q_1$ is represented by —$C(R_{13})(R_{14})$—, —$N(R_{15})$—, —N(—*)-, —S—, or —O—;

$Y_1$, $Y_2$, and $Y_3$ are each independently represented by —N=, —N(—*)-, —S—, —O—, —$C(R_{16})$=, or —C(—*)=;

$Z_1$, $Z_2$, $Ar_{12}$, $Ar_{13}$, $R_{13}$, $R_{14}$, $R_{15}$, and $R_{16}$ are each independently selected from the group consisting of a lone pair electron, a hydrogen atom, a heavy hydrogen atom, a halogen atom, a cyano group, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group;

$Ar_{11}$ is selected from the group consisting of a substituted or unsubstituted $C_1$-$C_{20}$ alkylene group, a substituted or unsubstituted $C_6$-$C_{20}$ arylene group, and a substituted or unsubstituted $C_3$-$C_{20}$ heteroarylene group;

p is an integer from 1 to 10;

r is an integer from 0 to 5; and

* indicates a binding site.

4. The compound of claim 1, wherein, in Formula 1, $R_1$ to $R_{12}$ are each independently one of Formulae 3a to 3d below:

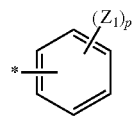

3a

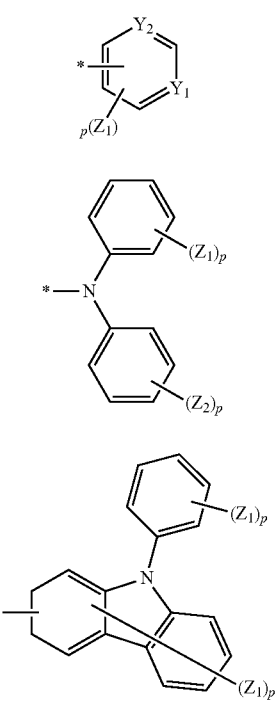
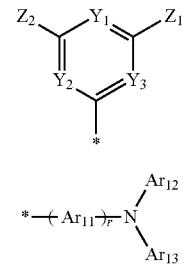
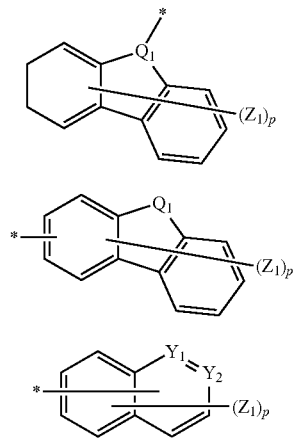

wherein, in Formulae 3a to 3d, $Y_1$ and $Y_2$ are each represented by —N= or —C($R_{16}$)=;

$Z_1$ and $Z_2$ are selected from the group consisting of a hydrogen atom, a heavy hydrogen atom, a halogen atom, a cyano group, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group;

p and q are each an integer from 1 to 5; and

* indicates a binding site.

5. The compound of claim 1, wherein the compound represented by Formula 1 is a symmetrical compound.

6. The compound of claim 1, wherein, in Formula 1, $R_1$ to $R_{12}$ are each independently selected from the group consisting of a hydrogen atom, a heavy hydrogen atom, a halogen atom, a cyano group, a substituted or unsubstituted $C_1$-$C_{20}$ alkyl group, a substituted or unsubstituted $C_1$-$C_{20}$ alkenyl group, and one of Formulae 2a to 2i below, and the compound represented by Formula 1 is a symmetrical compound:

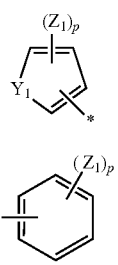

wherein, in Formulae 2a through 2i, $Q_1$ is represented by —C($R_{13}$)($R_{14}$)—, —N($R_{15}$)—, —N(—*)-, —S—, or —O—;

$Y_1$, $Y_2$, and $Y_3$ are each independently represented by —N=, —N(—*)-, —S—, —O—, —C($R_{16}$)=, or —C(—*)=;

$Z_1$, $Z_2$, $Ar_{12}$, $Ar_{13}$, $R_{13}$, $R_{14}$, $R_{15}$, and $R_{16}$ are each independently selected from the group consisting of a lone pair electron, a hydrogen atom, a heavy hydrogen atom, a halogen atom, a cyano group, a substituted or unsubstituted $C_1$-$C_{20}$ alkyl group, a substituted or unsubstituted $C_6$-$C_{20}$ aryl group, a substituted or unsubstituted $C_3$-$C_{20}$ heteroaryl group, a substituted or unsubstituted $C_6$-$C_{20}$ condensed polycyclic group, a halogen atom, a cyano group, a nitro group, a hydroxy group, and a carboxyl group;

$Ar_{11}$ is selected from the group consisting of a substituted or unsubstituted $C_1$-$C_{20}$ alkylene group, a substituted or unsubstituted $C_6$-$C_{20}$ arylene group, and a substituted or unsubstituted $C_3$-$C_{20}$ heteroarylene group;

p is an integer from 1 to 10;

r is an integer from 0 to 5; and

* indicates a binding site.

7. The compound of claim 1, wherein the compound represented by Formula 1 comprises one of Compounds below:
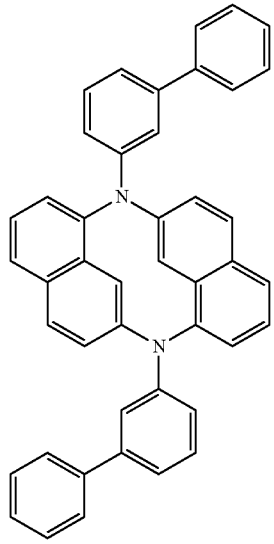
4
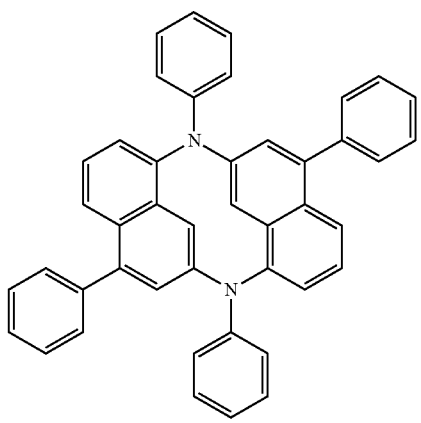
17
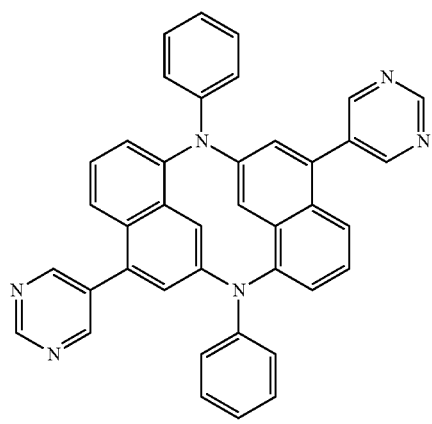
21
-continued
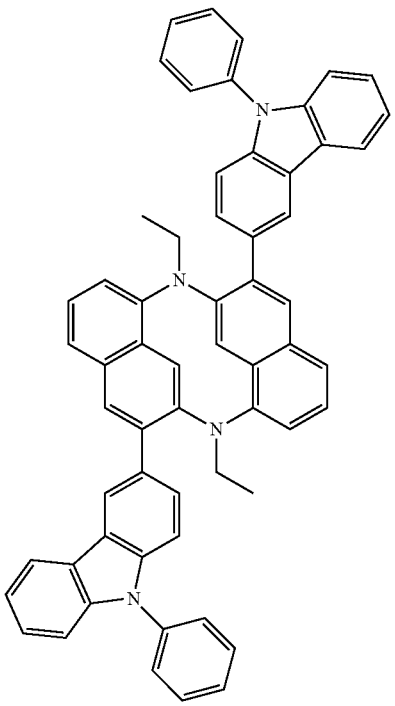
29
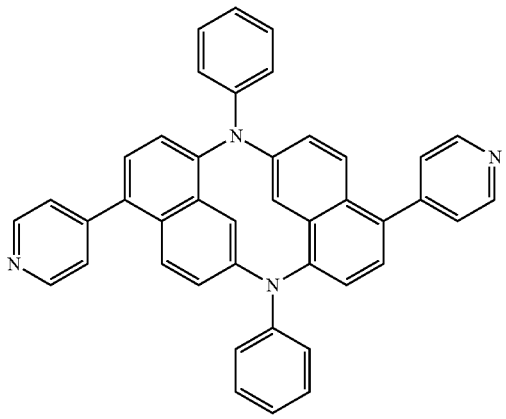
37
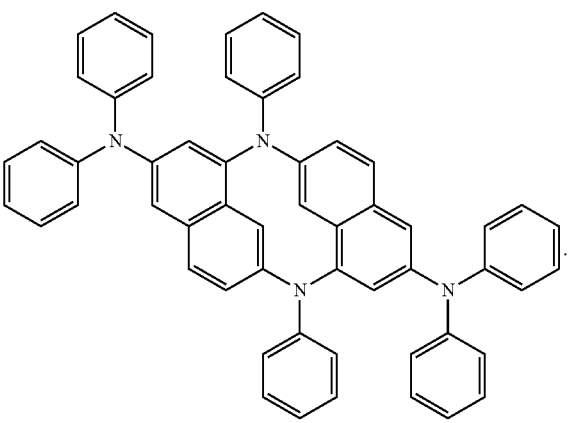
44

8. An organic light-emitting device comprising:
a first electrode;
a second electrode; and
an organic layer interposed between the first electrode and the second electrode, the organic layer comprising a first layer comprised of the compound represented by Formula 1 of claim 1.

9. The organic light-emitting device of claim 8, wherein the first layer comprises a hole injection layer (HIL), a hole transport layer (HTL), a functional layer having both hole injecting and hole transporting capabilities, an electron injection layer (EIL), an electron transporting layer (ETL), or a functional layer having both electron injecting and electron transporting capabilities.

10. The organic light-emitting device of claim 8, wherein the first layer is a light-emitting layer (EML), and the compound represented by Formula 1 is used as a host for a fluorescence or phosphorescence device.

11. The organic light-emitting device of claim 8, wherein the organic layer comprises a light emitting layer (EML), a hole transporting layer (HTL), and an electron transporting layer (ETL), the first layer is the EML, and the EML further comprises an anthracene compound, an arylamine compound, or a styryl compound.

12. The organic light-emitting device of claim 8, wherein the organic layer comprises a light emitting layer (EML), a hole transporting layer (HTL), and an electron transporting layer (ETL), the first layer is the EML, and the EML includes at least one of a red layer, a green layer, a blue layer, and a white layer, and any one of the red layer, the green layer, the blue layer, and the white layer of the EML further comprises a phosphorescent compound.

13. The organic light-emitting device of claim 8, wherein the first layer is a blue light emitting layer (EML).

14. The organic light-emitting device of claim 8, wherein the first layer is a blue light emitting layer (EML); and the compound represented by Formula 1 is used as a blue host.

15. The organic light-emitting device of claim 8, wherein the organic layer comprises a hole injection layer (HIL), a hole transporting layer (HTL), a functional layer having both hole injecting and hole transporting capabilities, a light emitting layer (EML), a hole blocking layer (HBL), an electron transporting layer (ETL), an electron injection layer (EIL), or a combination of at least two thereof.

16. The organic light-emitting device of claim 15, wherein at least one of the HIL, the HTL, and the functional layer having both hole injecting and hole transporting capabilities comprises a charge-generating material.

17. The organic light-emitting device of claim 15, wherein the ETL comprises an electron-transporting organic compound and a metal-containing material.

18. The organic light-emitting device of claim 17, wherein the metal-containing material comprises a lithium (Li) complex.

19. The organic light-emitting device of claim 8, wherein the first layer is formed by using a wet method using the compound represented by formula 1 below:

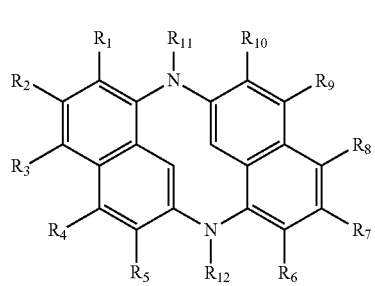

[Formula 1]

wherein, in Formula 1, $R_1$ through $R_{12}$ are each independently a hydrogen atom, a heavy hydrogen atom, a halogen atom, a cyano group, a substituted or unsubstituted $C_1$-$C_{60}$ alkyl group, a substituted or unsubstituted $C_1$-$C_{60}$ alkenyl group, a substituted or unsubstituted $C_6$-$C_{60}$ aryl group, an amino group substituted with a $C_6$-$C_{50}$ aryl group, a substituted or unsubstituted $C_3$-$C_{60}$ heteroaryl group, or a substituted or unsubstituted $C_6$-$C_{60}$ condensed polycyclic group, and wherein, optionally, adjacent substituents from among $R_1$ through $R_5$ or adjacent substituents from among $R_6$ through $R_{10}$ are connected to each other to form a ring.

20. A flat panel display device comprising the organic light-emitting device of claim 8, wherein the first electrode of the organic light-emitting device is electrically connected to a source electrode or a drain electrode of a thin film transistor.

* * * * *